US009029526B2

(12) United States Patent
Arnon et al.

(10) Patent No.: US 9,029,526 B2
(45) Date of Patent: May 12, 2015

(54) NUCLEIC ACID MOLECULES, POLYPEPTIDES, ANTIBODIES AND COMPOSITIONS FOR TREATING AND DETECTING INFLUENZA VIRUS INFECTION

(71) Applicant: Yeda Research and Development Co. Ltd., Rehovot (IL)

(72) Inventors: Ruth Arnon, Rechovot (IL); Sung-Ho Jeon, Suwon-si (KR); Basak Kayhan, Ankara (TR); Tamar Ben-Yedidia, Mazkeret Batya (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 109 days.

(21) Appl. No.: 13/680,132

(22) Filed: Nov. 19, 2012

(65) Prior Publication Data

US 2013/0079390 A1 Mar. 28, 2013

Related U.S. Application Data

(62) Division of application No. 12/585,600, filed on Sep. 18, 2009, now Pat. No. 8,357,789, which is a division of application No. 10/546,034, filed as application No. PCT/IL2004/000182 on Feb. 24, 2004, now Pat. No. 7,786,279.

(60) Provisional application No. 60/449,863, filed on Feb. 27, 2003.

(51) Int. Cl.
| | | |
|---|---|---|
| *C07H 21/02* | (2006.01) | |
| *C07H 21/00* | (2006.01) | |
| *A01N 43/04* | (2006.01) | |
| *A61K 48/00* | (2006.01) | |
| *C07H 21/04* | (2006.01) | |
| *C12N 15/115* | (2010.01) | |
| *G01N 33/569* | (2006.01) | |

(52) U.S. Cl.
CPC .............. *C07H 21/04* (2013.01); *C12N 15/115* (2013.01); *C12N 2310/16* (2013.01); *C12N 2310/322* (2013.01); *G01N 33/56983* (2013.01); *G01N 2333/11* (2013.01)

(58) Field of Classification Search
None
See application file for complete search history.

(56) References Cited

U.S. PATENT DOCUMENTS

| | | |
|---|---|---|
| 5,861,501 A | 1/1999 | Benseler et al. |
| 6,369,208 B1 | 4/2002 | Cole et al. |
| 2007/0059806 A1 | 3/2007 | Arnon et al. |

FOREIGN PATENT DOCUMENTS

| | | |
|---|---|---|
| JP | 11-506756 | 6/1999 |
| WO | WO 88/04932 | 7/1988 |
| WO | WO 92/14843 | 9/1992 |
| WO | WO 96/40159 | 12/1996 |
| WO | WO 97/03085 | 1/1997 |
| WO | WO 2004/076621 | 9/2004 |

OTHER PUBLICATIONS

Examiner's Report Dated Feb. 19, 2010 From the Australian Government, IP Australia Re.: Application No. 2004215133.
Examiner's Report Dated Jan. 13, 2009 From the Australian Government, IP Australia Re.: Application No. 2004215133.
International Preliminary Report on Patentability Dated Mar. 23, 2006 From the International Bureau of WIPO Re.: Application No. PCT/IL2004/000182.
Official Action Dated May 12, 2008 From the US Patent and Trademark Office Re.: U.S. Appl. No. 10/546,034.
Communication Pursuant to Article 94(3) EPC Dated Jul. 8, 2010 From the European Patent Office Re.: Application No. 04713970.4.
Communication Pursuant to Article 94(3) EPC Dated May 25, 2011 From the European Patent Office Re.: Application No. 04713970.4.
Communication Pursuant to Article 94(3) EPC Dated Dec. 27, 2011 From the European Patent Office Re.: Application No. 04713970.4.
International Search Report Dated Feb. 22, 2006 From the International Search Report Re.: Application No. PCT/IL04/00182.
Office Action Dated Oct. 7, 2008 From the Israeli Patent Office Re.: Application No. 170307 and Its Translation Into English.
Official Action Dated Jan. 12, 2012 From the US Patent and Trademark Office Re. U.S. Appl. No. 12/585,600.
Official Action Dated Jan. 15, 2008 From the US Patent and Trademark Office Re.: U.S. Appl. No. 10/546,034.
Official Action Dated Dec. 23, 2008 From the US Patent and Trademark Office Re.: U.S. Appl. No. 10/546,034.
Requisition by the Examiner Dated May 10, 2011 From the Canadian Intellectual Property Office Re. Application No. 2,517,074.
Response Dated Aug. 5, 2010 to Official Decision of Rejection of Apr. 16, 2010 From the Japanese Patent Office Re.: Application No. 2006-502644.
Summons to Attend Oral Proceedings Pursuant to Rule 115(1) EPC Dated Nov. 16, 2012 From the European Patent Office Re.: Application No. 04713970.4.
Supplementary European Search Report Dated Feb. 19, 2010 From the European Patent Office Re.: Application No. 04713970.4.

(Continued)

*Primary Examiner* — Amy Bowman

(57) ABSTRACT

Polynucleotides and polypeptides which participate in influenza virus infection of cells and nucleic acid molecules, which include a polynucleotide sequence capable of specifically binding the polypeptides of the present invention. Also provided are methods of using such nucleic acid molecules, polynucleotides and antibodies directed thereagainst for diagnosing, treating and preventing influenza virus infection.

12 Claims, 19 Drawing Sheets

(3 of 19 Drawing Sheet(s) Filed in Color)

(56) References Cited

OTHER PUBLICATIONS

Translation of Notice of Reason for Rejection Dated Nov. 2, 2012 From the Japanese Patent Office Re. Application No. 2010-180666.
Translation of Notice of Reason for Rejection Dated Oct. 27, 2009 From the Japanese Patent Office Re.: Application No. 2006-502644.
Translation of Official Query Dated Apr. 10, 2012 From the Japanese Patent Office Re.: Application No. 2006-502644.
Written Opinion Dated Feb. 22, 2006 From the International Searching Authority Re.: Application No. PCT/IL04/00182.
Brody et al. "Aptamers as Therapeutic and Diagnostic Agents", Reviews in Molecular Biotechnology, XP009031105, 74(1): 5-13, Mar. 1, 2000.
Cerchia et al. "Nucleic Acid Aptamers in Cancer Medicine", FEBS Letters, XP026978460, 528(1-3): 12-16, Sep. 25, 2002.
Cianci et al. "Differential Effect of Modified Capped RNA Substrates on Influenza Virus Transcription", Virus Research, 50: 65-75, 1997.
Clark et al. "Aptamers as Analytical Reagents", Electrophoresis, XP002364120, 23(9): 1335-1340, May 1, 2002.
Collett et al. "Functional RNA Microarrays for High-Throughput Screening of Antiprotein Aptamers", Analytical Biochemistry, 338: 113-123, 2005.
Edwards et al. "A Haemagglutinin (HA1)-Specific Fab Neutralizes Influenza A Virus by Inhibiting Fusion Activity", Journal of General Virology, 82: 1387-1395, 2001.
Edwards et al. "Hemagglutinin 1-Specific Immunoglobulin G and Fab Molecules Mediate Postattachment Neutralization of influenza a Virus by Inhibition of an Early Fusion Event", Journal of Virology, 75(21): 10208-10218, 2001.
Ellington et al. "In Vitro Selection of RNA Molecules That Bind Specific Ligands", Nature, 346(6287): 818-822, 1990.
Famulok et al. "Nucleic Acid Aptamers—From Selection In Vitro to Applications In Vivo", Accounts of Chemical Research, XP002221277, 33(9): 591-599, Sep. 1, 2000.
Gold "The Selex Process: A Surprising Source of Therapeutic and Diagnostic Compounds", The Harvey Lectures, XP009033532, Series 91: 47-57, Jan. 1, 1995.
Hesselberth et al. "In Vitro Selection of Nucleic Acids for Diagnostic Applications", Reviews in Molecular Biotechnology, 74: 15-25, 2000.
Jayasena "Aptamers: An Emerging Class of Molecules That Rival Antibodies in Diagnostics", Clinical Chemistry, XP008067440, 45(9): 1628-1650, Sep. 1, 1999.
Jeon et al. "Immunization With Influenza Virus Hemagglutinin Globular Region Containing the Receptor-Binding Pocket", Viral Immunology, XP002459084, 15(1): 165-176, Jan. 1, 2002.
Kim et al. "Selection and Stabilization of the RNA Aptamers Against the Human Immunodeficiency Virus Type-1 Nucleocapsid Protein", Biochemical and Biophysical Research Communications, 291(4): 925-931, 2002.
Kumar et al. "Isolation of RNA Aptamers Specific to the NS3 Protein of Hepatitis C Virus From a Pool of Completely Random RNA", Virology, 237(2): 270-282, 1997.
Lee et al. "Definition of the Minimal Viral Components Required for the Initiation of Unprimed RNA Synthesis by Influenza Virus RNA Polymerase", Nucleic Acids Research, XP002995151, 30(2): 429-438, 2002.
Li et al. "Typing and Subtyping Influenza Virus Using DNA Microarrays and Mutiplex Reverse Transcriptase PCR", Journal of Clinical Microbiology,39(2): 696-704, 2001.
Müller et al. "Anti-Influenza Response Achieved by Immunization With a Synthetic Conjugate", Proc. Natl. Acad. Sci. USA, 79: 569-573, 1982.
Osborne et al. "Aptamers as Therapeutic and Diagnostic Reagents: Problems and Prospects", Current Opinion in Chemical Biology, 1: 5-9, 1997.
Pan et al. "Isolation of Virus-Neutralizing RNAs From a Large Pool of Random Sequences", Proc. Natl. Acad. Sci. USA, 92(25): 11509-11513, Dec. 1995.
Skehel et al. "Receptor Binding and Membrane Fusion in Virus Entry: The Influenza Hemagglutinin", Annual Reviews in Biochemistry, 69: 531-569, 2000.
Sun "Technology Evaluation: SELEX, Gileas Sciences Inc", Current Opinion in Molecular Therapeutics, XP008042332, 2(1): 100-105, Jan. 1, 2000.
Wilson et al. "Structure of the Haemagglutinin Membrane Glycoprotein of Influenza Virus at 3 Å Resolution", Nature, 289: 366-373, 1981.

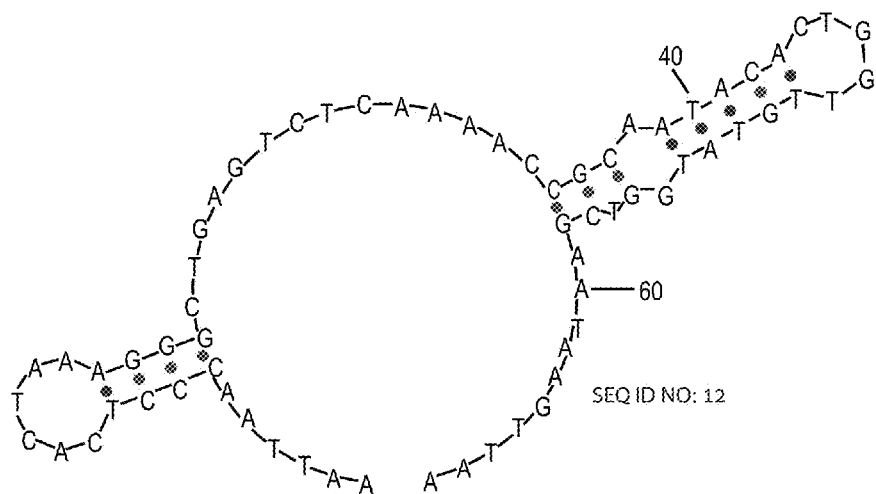
FIG. 2C
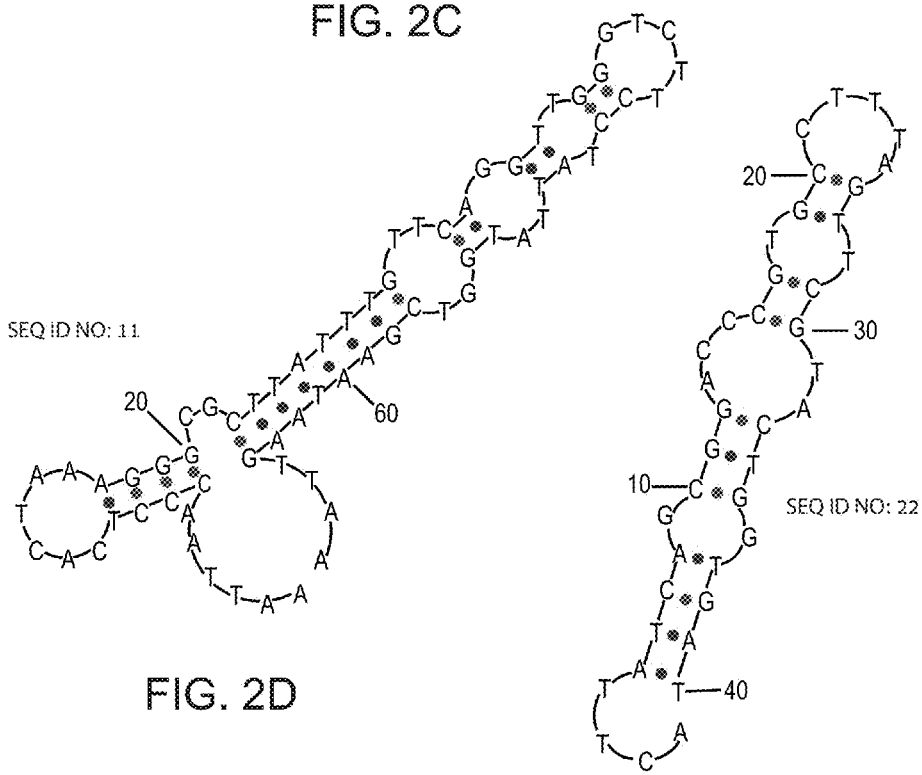
FIG. 2D
FIG. 2E

| MDCK infected | MDCK infected+A22 SEQ ID NO: 12 | MDCK+A22 SEQ ID NO: 12 | |
|---|---|---|---|
| Fig. 4a | Fig. 4b | Fig. 4c | Culture viewed by light microscope |
| Fig. 4d | Fig. 4e | Fig. 4f | Immunoflourescence staining |

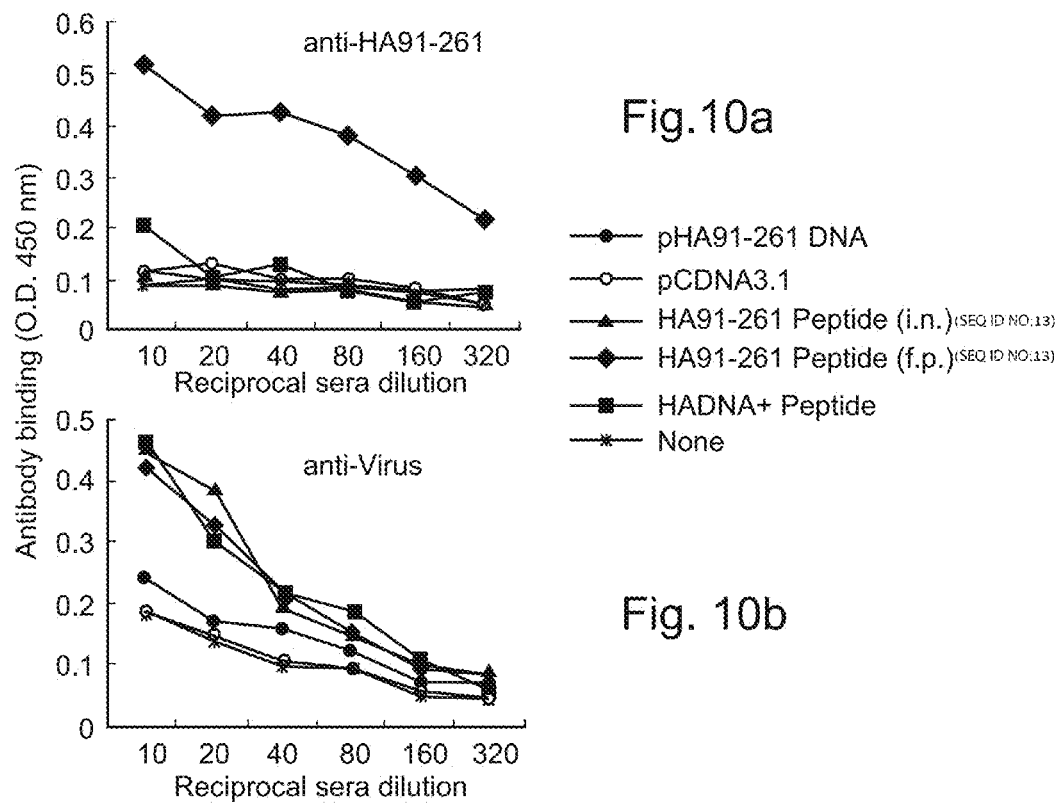
Fig. 10a
Fig. 10b
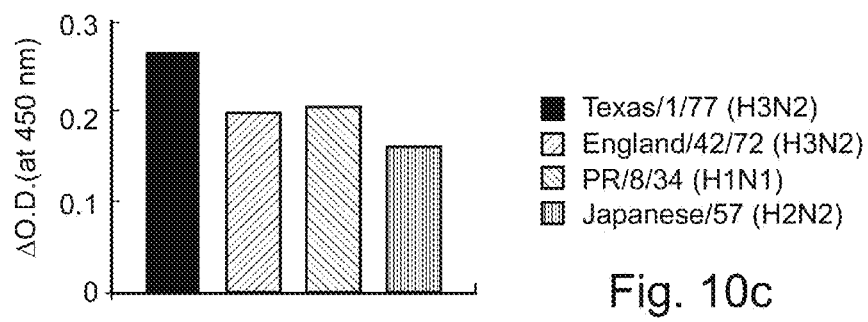
Fig. 10c

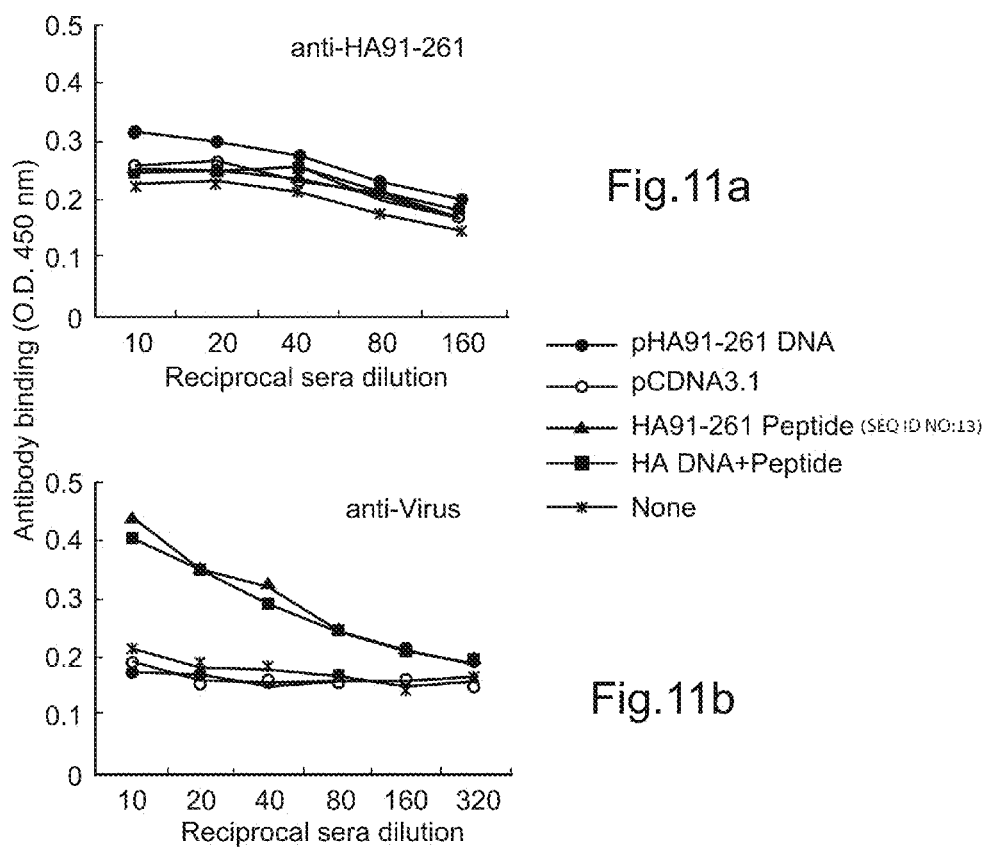

SEQUENCE LISTING

```
<160> NUMBER OF SEQ ID NOS: 23

<210> SEQ ID NO 1
<211> LENGTH: 329
<212> TYPE: PRT
<213> ORGANISM: Influenza A virus

<400> SEQUENCE: 1
```

Gln Asp Phe Pro Gly Asn Asp Asn Ser Thr Ala Thr Leu Cys Leu Gly
 1               5                  10                  15

His His Ala Val Pro Asn Gly Thr Leu Val Lys Thr Ile Thr Asn Asp
             20                  25                  30

Gln Ile Glu Val Thr Asn Ala Thr Glu Leu Val Gln Ser Ser Ser Thr
         35                  40                  45

Gly Lys Ile Cys Asn Asn Pro His Arg Ile Leu Asp Gly Ile Asn Cys
     50                  55                  60

Thr Leu Ile Asp Ala Leu Leu Gly Asp Pro His Cys Asp Gly Phe Gln
 65                  70                  75                  80

Asn Glu Thr Trp Asp Leu Phe Val Glu Arg Ser Lys Ala Phe Ser Asn
                 85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Asn Glu Gly Phe Thr Trp Thr
        115                 120                 125

Gly Val Thr Gln Asn Gly Gly Ser Asn Ala Cys Lys Arg Gly Pro Asp
    130                 135                 140

Ser Gly Phe Phe Ser Arg Leu Asn Trp Leu Tyr Lys Ser Gly Ser Ala
145                 150                 155                 160

Tyr Pro Val Leu Asn Val Thr Met Pro Asn Asn Asp Asn Phe Asp Lys
                165                 170                 175

Leu Tyr Ile Trp Gly Val His His Pro Ser Thr Asp Gln Glu Gln Thr
            180                 185                 190

Asn Leu Tyr Val Gln Ala Ser Gly Arg Val Thr Val Ser Thr Lys Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Ile Leu Val Ile Asn Ser Asn Gly Asn Leu Ile Ala Pro Arg Gly

```
                        245                 250                 255

Tyr Phe Lys Met Arg Thr Gly Lys Ser Ser Ile Met Arg Ser Asp Ala
            260                 265                 270

Pro Ile Gly Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 2
<211> LENGTH: 18
<212> TYPE: PRT
<213> ORGANISM: Artificial sequence
<220> FEATURE:
<223> OTHER INFORMATION: Synthetic peptide

<400> SEQUENCE: 2

Ser Lys Ala Phe Ser Asn Cys Tyr Pro Tyr Asp Val Pro Asp Tyr Ala
1               5                   10                  15

Ser Leu

<210> SEQ ID NO 3
<211> LENGTH: 13
<212> TYPE: PRT
<213> ORGANISM: Artificial sequence
<220> FEATURE:
<223> OTHER INFORMATION: Synthetic peptide

<400> SEQUENCE: 3

Pro Lys Tyr Val Lys Gln Asn Thr Leu Lys Leu Ala Thr
1               5                   10

<210> SEQ ID NO 4
<211> LENGTH: 19
<212> TYPE: PRT
<213> ORGANISM: Artificial sequence
<220> FEATURE:
<223> OTHER INFORMATION: Synthetic peptide

<400> SEQUENCE: 4

Cys Pro Lys Tyr Val Lys Gln Asn Thr Leu Lys Leu Ala Thr Gly Met
1               5                   10                  15

Arg Asn Val

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Ser Ala Ala Phe Glu Asp Leu Arg Val Leu Ser Phe Ile Arg Gly Tyr
1               5                   10                  15

<210> SEQ ID NO 6
<211> LENGTH: 14
<212> TYPE: PRT
<213> ORGANISM: Artificial sequence
<220> FEATURE:
```

<223> OTHER INFORMATION: Synthetic peptide

<400> SEQUENCE: 6

Glu Leu Arg Ser Arg Tyr Trp Ala Ile Arg Thr Arg Ser Gly
1               5                   10

<210> SEQ ID NO 7
<211> LENGTH: 17
<212> TYPE: PRT
<213> ORGANISM: Artificial sequence
<220> FEATURE:
<223> OTHER INFORMATION: Synthetic peptide

<400> SEQUENCE: 7

Gly Thr His Pro Arg Ser Ser Ala Gly Leu Lys Asn Asp Leu Leu Glu
1               5                   10                  15

Asn

<210> SEQ ID NO 8
<211> LENGTH: 26
<212> TYPE: PRT
<213> ORGANISM: Artificial sequence
<220> FEATURE:
<223> OTHER INFORMATION: Synthetic peptide

<400> SEQUENCE: 8

Phe Val Gln Asn Ala Leu Asn Gly Asn Gly Asp Pro Asn Asn Met Asp
1               5                   10                  15

Arg Ala Val Lys Leu Tyr Arg Lys Leu Lys
            20                  25

<210> SEQ ID NO 9
<211> LENGTH: 17
<212> TYPE: PRT
<213> ORGANISM: Artificial sequence
<220> FEATURE:
<223> OTHER INFORMATION: Synthetic peptide

<400> SEQUENCE: 9

Phe Thr Leu Thr Val Pro Ser Glu Arg Gly Leu Gln Arg Arg Arg Phe
1               5                   10                  15

Val

<210> SEQ ID NO 10
<211> LENGTH: 21
<212> TYPE: PRT
<213> ORGANISM: Artificial sequence
<220> FEATURE:
<223> OTHER INFORMATION: Synthetic peptide

<400> SEQUENCE: 10

Ala Thr Cys Glu Gln Ile Ala Asp Ser Gln His Arg Ser His Arg Gln
1               5                   10                  15

Met Val Ala Thr Thr
            20

<210> SEQ ID NO 11
<211> LENGTH: 68
<212> TYPE: RNA
<213> ORGANISM: Artificial sequence
<220> FEATURE:
<223> OTHER INFORMATION: Synthetic oligonucleotide

<400> SEQUENCE: 11
aauuaacccu cacuaaaggg cgcuuauuug uucagguugg gucuuccuau uauggucgaa    60
uaaguuaa    68

<210> SEQ ID NO 12
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 12
aattaaccct cactaaaggg ctgagtctca aaaccgcaat acactggttg tatggtcgaa    60
taagttaa    68

<210> SEQ ID NO 13
<211> LENGTH: 171
<212> TYPE: PRT
<213> ORGANISM: Artificial sequence
<220> FEATURE:
<223> OTHER INFORMATION: Synthetic peptide

<400> SEQUENCE: 13

Ser Lys Ala Phe Ser Asn Cys Tyr Pro Tyr Asp Val Pro Asp Tyr Ala
1               5                   10                  15

Ser Leu Arg Ser Leu Val Ala Ser Ser Gly Thr Leu Glu Phe Ile Asn
            20                  25                  30

Glu Gly Phe Thr Trp Thr Gly Val Thr Gln Asn Gly Gly Ser Asn Ala
        35                  40                  45

Cys Lys Arg Gly Pro Asp Ser Gly Phe Phe Ser Arg Leu Asn Trp Leu
    50                  55                  60

Tyr Lys Ser Gly Ser Ala Tyr Pro Val Leu Asn Val Thr Met Pro Asn
65                  70                  75                  80

Asn Asp Asn Phe Asp Lys Leu Tyr Ile Trp Gly Val His His Pro Ser
                85                  90                  95

Thr Asp Gln Glu Gln Thr Asn Leu Tyr Val Gln Ala Ser Gly Arg Val
            100                 105                 110

Thr Val Ser Thr Lys Arg Ser Gln Gln Thr Ile Ile Pro Asn Ile Gly
        115                 120                 125

Ser Arg Pro Trp Val Arg Gly Leu Ser Ser Arg Ile Ser Ile Tyr Trp
    130                 135                 140

Thr Ile Val Lys Pro Gly Asp Ile Leu Val Ile Asn Ser Asn Gly Asn
145                 150                 155                 160

Leu Ile Ala Pro Arg Gly Tyr Phe Lys Met Arg
                165                 170

<210> SEQ ID NO 14
<211> LENGTH: 146
<212> TYPE: PRT
<213> ORGANISM: Artificial sequence
<220> FEATURE:
<223> OTHER INFORMATION: Synthetic peptide

<400> SEQUENCE: 14

Gly Thr Leu Glu Phe Ile Asn Glu Gly Phe Thr Trp Thr Gly Val Thr
1               5                   10                  15

Gln Asn Gly Gly Ser Asn Ala Cys Lys Arg Gly Pro Asp Ser Gly Phe
            20                  25                  30

Phe Ser Arg Leu Asn Trp Leu Tyr Lys Ser Gly Ser Ala Tyr Pro Val
        35                  40                  45

```
Leu Asn Val Thr Met Pro Asn Asn Asp Asn Phe Asp Lys Leu Tyr Ile
    50                  55                  60

Trp Gly Val His His Pro Ser Thr Asp Gln Glu Gln Thr Asn Leu Tyr
 65                  70                  75                  80

Val Gln Ala Ser Gly Arg Val Thr Val Ser Thr Lys Arg Ser Gln Gln
                 85                  90                  95

Thr Ile Ile Pro Asn Ile Gly Ser Arg Pro Trp Val Arg Gly Leu Ser
                100                 105                 110

Ser Arg Ile Ser Ile Tyr Trp Thr Ile Val Lys Pro Gly Asp Ile Leu
            115                 120                 125

Val Ile Asn Ser Asn Gly Asn Leu Ile Ala Pro Arg Gly Tyr Phe Lys
        130                 135                 140

Met Arg
145

<210> SEQ ID NO 15
<211> LENGTH: 130
<212> TYPE: PRT
<213> ORGANISM: Artificial sequence
<220> FEATURE:
<223> OTHER INFORMATION: Synthetic peptide

<400> SEQUENCE: 15

Gly Thr Leu Glu Phe Ile Asn Glu Gly Phe Thr Trp Thr Gly Val Thr
  1               5                  10                  15

Gln Asn Gly Gly Ser Asn Ala Cys Lys Arg Gly Pro Asp Ser Gly Phe
                 20                  25                  30

Phe Ser Arg Leu Asn Trp Leu Tyr Lys Ser Gly Ser Ala Tyr Pro Val
             35                  40                  45

Leu Asn Val Thr Met Pro Asn Asn Asp Asn Phe Asp Lys Leu Tyr Ile
    50                  55                  60

Trp Gly Val His His Pro Ser Thr Asp Gln Glu Gln Thr Asn Leu Tyr
 65                  70                  75                  80

Val Gln Ala Ser Gly Arg Val Thr Val Ser Thr Lys Arg Ser Gln Gln
                 85                  90                  95

Thr Ile Ile Pro Asn Ile Gly Ser Arg Pro Trp Val Arg Gly Leu Ser
                100                 105                 110

Ser Arg Ile Ser Ile Tyr Trp Thr Ile Val Lys Pro Gly Asp Ile Leu
            115                 120                 125

Val Ile
    130

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
aattaaccct cactaaaggg                                             20

<210> SEQ ID NO 17
<211> LENGTH: 18
<212> TYPE: DNA
<213> ORGANISM: Artificial sequence
<220> FEATURE:
<223> OTHER INFORMATION: Single strand DNA oligonucleotide
```

```
<400> SEQUENCE: 17
tatggtcgaa taagttaa                                                  18

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
aattaaccct cactaaaggg                                                20

<210> SEQ ID NO 19
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 19
ttaacttatt cgaccata                                                  18

<210> SEQ ID NO 20
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 20
ggatccagca aagctttcag caactgt                                        27

<210> SEQ ID NO 21
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 21
gtcgacgcgc attttgaagt aaccccc                                        26

<210> SEQ ID NO 22
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 22
acttatcagc ggacccgtgc ctttagttcg tactggtgat                          40

<210> SEQ ID NO 23
<211> LENGTH: 68
<212> TYPE: DNA
<213> ORGANISM: Artificial sequence
<220> FEATURE:
<223> OTHER INFORMATION: Synthetic oligonucleotide

<400> SEQUENCE: 23
aattaaccct cactaaaggg cgcttatttg ttcaggttgg gtcttcctat tatggtcgaa    60
taagttaa                                                             68
```

NUCLEIC ACID MOLECULES, POLYPEPTIDES, ANTIBODIES AND COMPOSITIONS FOR TREATING AND DETECTING INFLUENZA VIRUS INFECTION

RELATED PATENT APPLICATIONS

This application is a divisional of U.S. patent application Ser. No. 12/585,600 filed on Sep. 18, 2009, which is a divisional of U.S. patent application Ser. No. 10/546,034 filed on Aug. 18, 2005, now U.S. Pat. No. 7,786,279, which is a National Phase of PCT Patent Application No. PCT/IL2004/000182 having International Filing Date of Feb. 24, 2004, which claims the benefit of priority of U.S. Provisional Application No. 60/449,863 filed on Feb. 27, 2003. The contents of the above application are all incorporated herein by reference.

FIELD AND BACKGROUND OF THE INVENTION

The present invention relates to nucleic acid molecules, polypeptides, antibodies and pharmaceutical composition containing same, which can be utilized for treating and detecting influenza virus infection in vertebrates such as avian, swines and humans.

Influenza viruses have been a major cause of mortality and morbidity in man throughout recorded history. Influenza epidemics occur at regular intervals, which vary widely in severity but which always cause significant mortality and morbidity, most frequently in the elderly population. An influenza infection produces an acute set of symptoms including headache, cough, fever and general malaise. In severe cases or situations involving pre-existing pulmonary or cardiovascular disease, hospitalization is required. Pneumonia due to direct viral infection or due to secondary bacterial or viral invasion is the most frequent complication. For a review on the clinical aspects of influenza virus infection see Douglas (1990) New England Journal of Medicine, 322:443-450.

Influenza viruses are currently divided into three types: A, B, and C, based upon differences in internal antigenic proteins; while the A and B types are closely related and account for most infections, the type C influenza virus represents a distant third in disease-causing potential and is probably of little public health concern. Although overall gene homology is less than 30%, between the A and B types, these viruses share a common ancestor and include eight RNAs of negative sense polarity. Hemagglutinin (HA) and neuraminidase (NA) are expressed on the surface of the lipid containing virus particles and are primarily responsible for the antigenic changes observed in influenza viruses.

New strains of influenza caused by antigenic drift appear at regular frequency, usually annually, and begin a cycle of infection, which travels around the globe. Little is known about how individual epidemics are initiated. Major new subtypes of influenza appear less frequently but can result in major pandemics.

It will be appreciated that up to 20% of the population may develop influenza infection in any given year and influenza epidemics are responsible for 20,000 deaths per year in the U.S. [Palese (2002) J. Clin. Invest. 110:9-13]. By far the most catastrophic impact of influenza during the past 100 years was the pandemic of 1918, which cost more than 500,000 lives in the U.S. and lowered life expectancy by almost 10 years [Heilman (1990) Clin. North Am. 37:669-688].

Given the impact of influenza on individuals and on society the challenge at present is to generate highly potent prophylactic tools which can be used to prevent influenza infection in subjects which are at considerable risk of infection such as young children and the elderly population.

Several approaches have been undertaken to uncover novel anti influenza agents.

Inactivated influenza virus vaccines—The most effective way to deal with the influenza virus for a population at risk of severe complications is by prevention. To be effective, current vaccines must contain an A, B and preferably C virus components. To prepare vaccines, the viral strains are grown in embryonated eggs, and the virus is then purified and made noninfectious by chemical inactivation. Use of the available influenza vaccine is an effective way to lower the mortality in a population, however due to the ever-changing nature of the virus, the development of a vaccine with the appropriate composition to protect against the currently circulating virus strains is complex and expensive. Moreover, patient compliance in receiving the vaccine is generally very low. Thus, large numbers of patients at risk of serious complications from influenza virus go unprotected.

Cold adapted influenza virus vaccines—The generation of temperature sensitive influenza viruses as live vaccines has been attempted because the pathogenicity in animals and mammals is significantly attenuated [Wareing (2001) Vaccine 19:3320-3330; Maasab (1990) Adv. Biotechnol. Processes 14:203-242]. Typically, to generate cold adapted viruses the influenza viruses are passaged in chicken kidney cells and in embryonated eggs to adapt growth thereof at 25° C. Thus, the annually adapted vaccine formulations can be genetically engineered to include the two genes which encode major viral surface antigens (i.e., HA and NA) reflecting the antigens found in current strains, whereas the remaining six genes derived from the cold-adapted master strains. Such live-virus vaccines can induce local neutralizing immunity and cell-mediated immune responses, which may be associated with a longer lasting and cross-reactive immunity than is elicited by chemically inactivated virus preparations. However, the use of live vaccines requires extensive monitoring against unexpected complications, which might arise from the spread of virulent revertants essentially explaining the nonexistence of licensure for such therapy in the U.S.

Genetically engineered live influenza virus vaccines—The advent of techniques for engineering site-specific changes in the genomes of RNA viruses rendered it possible to develop new vaccine approaches [Enami (1990) Proc. Natl. Acad. Sci. USA 87:3802-3805; Garcia-Sastre (1998) Trends. Biotechnol. 16:230-235]. Thus, generation of virus particles which undergo only a single cycle of replication has been demonstrated by Watanbe and co-workers [(2002), J. Virol. 76:767-773]. Infection of cells with a preparation of virus particles lacking the NEP expressing gene (NS2) produces viral proteins but does not result in the formation of infectious particles. Thus, these preparations induce a protective antibody response and stimulate a strong cell-mediated immune response without allowing the replication of infectious virus. Another approach for virus attenuation is the generation of a replication defective strain which M2 gene is eliminated. Such a deletion mutant grows efficiently in tissue culture but only poorly in mice and thus represents a potential live virus vaccine candidate [Watanbe (2001) J. Virol. 75:5656-5662]. However, frequently the infectious titers of such engineered viruses are too low to be useful in a clinical setting.

DNA vaccination—This approach involves the topical administration or administration via injection of plasmid DNA encoding one or more influenza proteins. However, to date reports on DNA vaccination against influenza have been limited to studies in animal models and no therapeutic efficacy has been demonstrated in human subjects [Donnelly (1995) Nat. Med. 1:583-587; Ljungberg (2000) 268:244-25-; Kodihalli (2000) Vaccine 18:2592-2599].

Antiviral agents—Four antiviral agents are approved at present in the U.S.; amantidine and rimantidine are chemically related inhibitors of the ion channel M2 protein which is involved in viral uncoating [Hay (1985) EMBO J 4:3021-3024], and zanamivir and oseltamivir are NA inhibitors [Palese (1976) J. Gen. Virol. 33:159-63], preventing the proper release of influenza virus particles from the cytoplasmic membrane. These antiviral drugs are important adjuncts for any medical intervention against influenza, and may be used in prophylaxis against the virus (excluding zanamivir which has not yet been approved). Furthermore, these agents can be of significant value in case a new pandemic strain emerge against which a vaccine has not been developed.

Despite overall advantages, the widespread use of currently available antiviral agents is limited by concerns over side effects, patients compliance and the possible emergence of drug-resistant variants.

Antisense—Attempts at the inhibition of influenza virus using antisense oligonucleotides have been reported. Leiter and co-workers have targeted phosphodiester and phosphorothioate oligonucleotides to influenza A and influenza C viruses. Leiter, J., Agrawal, S., Palese, P. & Zamecnik, P. C., Proc. Natl. Acad. Sci. USA, 87:3430-3434 (1990). In this study polymerase PB1 gene and mRNA were targeted in the vRNA 3' region and mRNA 5' region, respectively. Sequence-specific inhibition of influenza A was not observed although some specific inhibition of influenza C was noted. No other influenza virus segments or mRNAs were targeted.

There is thus a widely recognized need for, and it would be highly advantageous to have compositions, which can be used to diagnose and treat influenza virus infection devoid of the above limitations.

SUMMARY OF THE INVENTION

According to one aspect of the present invention there is provided a nucleic acid molecule comprising a polynucleotide sequence capable of specifically binding a polypeptide participating in influenza virus infection of cells.

According to further features in preferred embodiments of the invention described below, the polynucleotide sequence is selected from the group consisting of SEQ ID Nos. 11 and 12.

According to still further features in the described preferred embodiments the polypeptide is an influenza virus polypeptide.

According to still further features in the described preferred embodiments the polynucleotide sequence is capable of binding a region of hemagglutinin defined by amino acid coordinates 91-261 of SEQ ID NO: 1.

According to still further features in the described preferred embodiments the polypeptide is a host cell polypeptide.

According to still further features in the described preferred embodiments the host cell polypeptide is a sialic acid receptor.

According to another aspect of the present invention there is provided a method of generating a molecule capable of inhibiting influenza virus infection, the method comprising: (a) contacting a plurality of nucleic acid molecules with a polypeptide participating in influenza virus infection of cells; (b) identifying at least one nucleic acid molecule from the plurality of nucleic acid molecules capable of specifically binding the polypeptide; and (c) isolating the at least one nucleic acid molecule capable of binding the polypeptide, thereby generating the molecule capable of inhibiting influenza virus infection.

According to still further features in the described preferred embodiments the method further comprising generating the plurality of nucleic acid molecules using a combinatorial synthesis approach prior to (a).

According to still further features in the described preferred embodiments the method further comprising modifying the plurality of nucleic acid molecules prior to (a) or following (c).

According to still further features in the described preferred embodiments the method further comprising repeating steps (a) to (c).

According to yet another aspect of the present invention there is provided a pharmaceutical composition comprising a nucleic acid molecule including a polynucleotide sequence capable of specifically binding a polypeptide participating in influenza virus infection of cells and a physiologically acceptable carrier.

According to still another aspect of the present invention there is provided an article-of-manufacture comprising packaging material and a pharmaceutical composition identified for treating or preventing influenza infection being contained within the packaging material, the pharmaceutical composition including, as an active ingredient, a nucleic acid molecule including a polynucleotide sequence capable of specifically binding a polypeptide participating in influenza virus infection of cells.

According to an additional aspect of the present invention there is provided a method of treating or preventing influenza virus infection comprising providing to a subject in need thereof, a therapeutically effective amount of a nucleic acid molecule including a polynucleotide sequence capable of specifically binding a polypeptide participating in influenza virus infection of cells, thereby treating or preventing the influenza virus infection.

According to still further features in the described preferred embodiments the providing is effected by: (i) administering of the nucleic acid molecule; and/or (ii) administering a polynucleotide expressing the nucleic acid molecule.

According to yet an additional aspect of the present invention there is provided a method of identifying influenza virus in a biological sample, the method comprising: (a) contacting the biological sample with a nucleic acid molecule including a polynucleotide sequence capable of specifically binding an influenza virus polypeptide; and (b) detecting the nucleic acid molecule bound to the influenza virus polypeptide in the biological sample, to thereby identify the influenza infection.

According to still an additional aspect of the present invention there is provided a method of targeting an antiviral agent to an influenza virus infected tissue, the method comprising administering to a subject in need thereof a therapeutic effective amount of the antiviral agent conjugated to a nucleic acid molecule including a polynucleotide sequence capable of specifically binding an influenza virus polypeptide, thereby targeting the antiviral agent to the influenza infected tissue.

According to a further aspect of the present invention there is provided a composition of matter comprising an antiviral agent conjugated to a nucleic acid molecule including a polynucleotide sequence capable of specifically binding a polypeptide participating in influenza virus infection of cells.

According to still further features in the described preferred embodiments wherein the polypeptide is an influenza virus polypeptide.

According to still further features in the described preferred embodiments the polypeptide is selected from the group consisting of hemagglutinin, neuraminidase, RNA-directed RNA polymerase core proteins, M1 matrix protein, M2 matrix protein and NS proteins.

According to still further features in the described preferred embodiments the polynucleotide sequence is capable of binding a region of hemagglutinin defined by amino acid coordinates 91-261 of SEQ ID NO: 1.

According to still further features in the described preferred embodiments the polypeptide is a host cell polypeptide.

According to still further features in the described preferred embodiments the host cell polypeptide is a sialic acid receptor.

According to still further features in the described preferred embodiments the polynucleotide sequence is single stranded.

According to still further features in the described preferred embodiments the polynucleotide sequence is DNA.

According to still further features in the described preferred embodiments the polynucleotide sequence is RNA.

According to still further features in the described preferred embodiments the nucleic acid molecule further comprising a detectable label.

According to still further features in the described preferred embodiments the polynucleotide sequence includes 2'-fluoro (2'-F) modified nucleotides.

According to still further features in the described preferred embodiments the polynucleotide sequence is selected having a length between 10 to 35 nucleotides.

According to still further features in the described preferred embodiments the pharmaceutical composition further includes an agent.

According to still further features in the described preferred embodiments agent is selected from the group consisting of an immunomodulatory agent, an antibiotic, an antiviral agent, an antisense molecule and a rybosyme.

According to yet a further aspect of the present invention there is provided a polypeptide useful for vaccination against influenza virus, the polypeptide comprising an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided a pharmaceutical composition comprising a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, the polypeptide not including the HA2 domain of influenza virus and a pharmaceutically acceptable carrier or diluent.

According to still a further aspect of the present invention there is provided an antibody or antibody fragment comprising an antigen binding site specifically recognizing a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided an isolated polynucleotide encoding a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided a nucleic acid construct comprising the isolated polynucleotide encoding a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided a host cell comprising the nucleic acid construct.

According to still a further aspect of the present invention there is provided a pharmaceutical composition comprising a polynucleotide encoding a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, the polypeptide not including the HA2 domain of influenza virus and a pharmaceutically acceptable carrier or diluent.

According to still a further aspect of the present invention there is provided a method of treating or preventing influenza virus infection comprising providing to a subject in need thereof, a therapeutically effective amount of a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided a method of treating or preventing influenza virus infection comprising providing to a subject in need thereof, a therapeutically effective amount of an antibody or antibody fragment including an antigen binding site specifically recognizing a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus.

According to still a further aspect of the present invention there is provided a method of identifying influenza virus in a biological sample, the method comprising: (a) contacting the biological sample with an antibody or antibody fragment including an antigen binding site specifically recognizing a polypeptide including an amino acid sequence being at least 60% homologous to SEQ ID NO: 13 as determined using the BestFit software of the Wisconsin sequence analysis package, utilizing the Smith and Waterman algorithm, where gap creation penalty equals 8 and gap extension penalty equals 2, wherein the polypeptide does not include the HA2 domain of influenza virus; and (b) detecting immunocomplexes including the antibody or antibody fragment in the biological sample, to thereby identify the influenza virus in the biological sample.

According to still further features in the described preferred embodiments the polypeptide is as set forth in SEQ ID NOs. 13-15.

According to still further features in the described preferred embodiments the amino acid sequence is as set forth in SEQ ID NOs. 13-15.

According to still further features in the described preferred embodiments the amino acid sequence is defined by amino acid coordinates 91-261 of SEQ ID NO: 1.

According to still further features in the described preferred embodiments the amino acid sequence is defined by amino acid coordinates 116-261 of SEQ ID NO: 1.

According to still further features in the described preferred embodiments the amino acid sequence is defined by amino acid coordinates 116-245 of SEQ ID NO: 1.

According to still further features in the described preferred embodiments the antibody or antibody fragment further includes a label.

According to still further features in the described preferred embodiments the detecting the immunocomplexes is effected by quantifying intensity of the label following (b).

According to still a further aspect of the present invention there is provided a nucleic acid molecule as set forth in SEQ ID NO: 11 or 12.

The present invention successfully addresses the shortcomings of the presently known configurations by providing nucleic acid molecules, polypeptides, antibodies generated thereagainst and compositions containing the same which can be used to diagnose and treat influenza virus infection.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
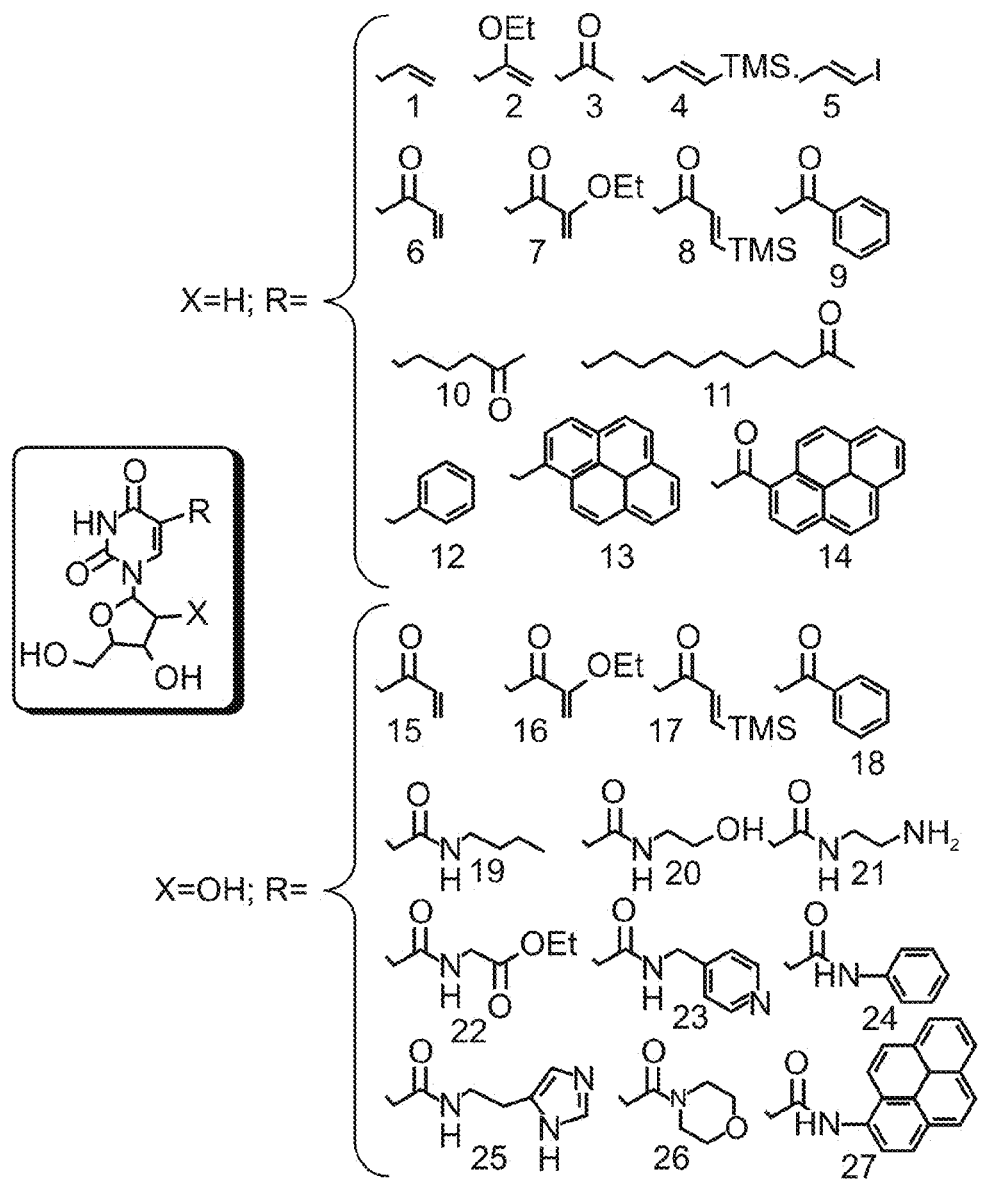
Figure 1B:
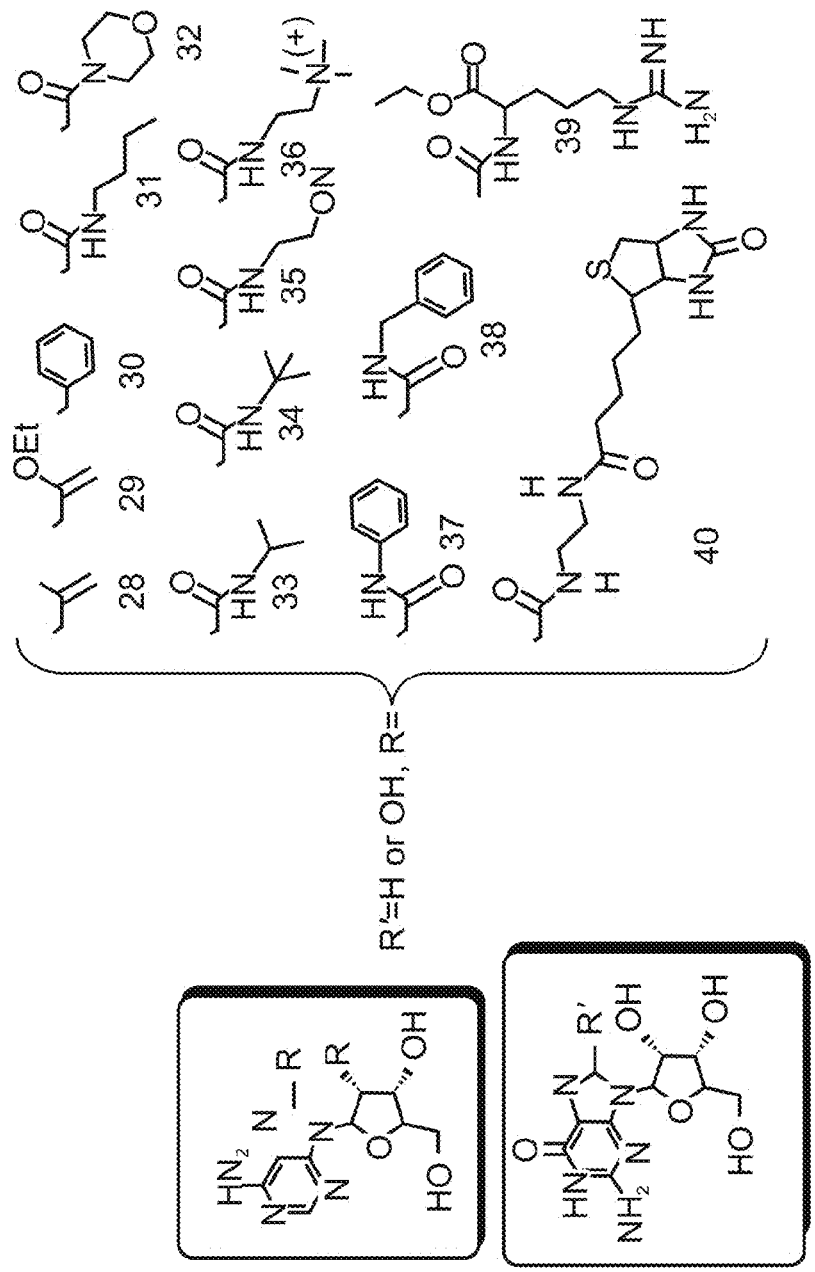
Figure 1C:
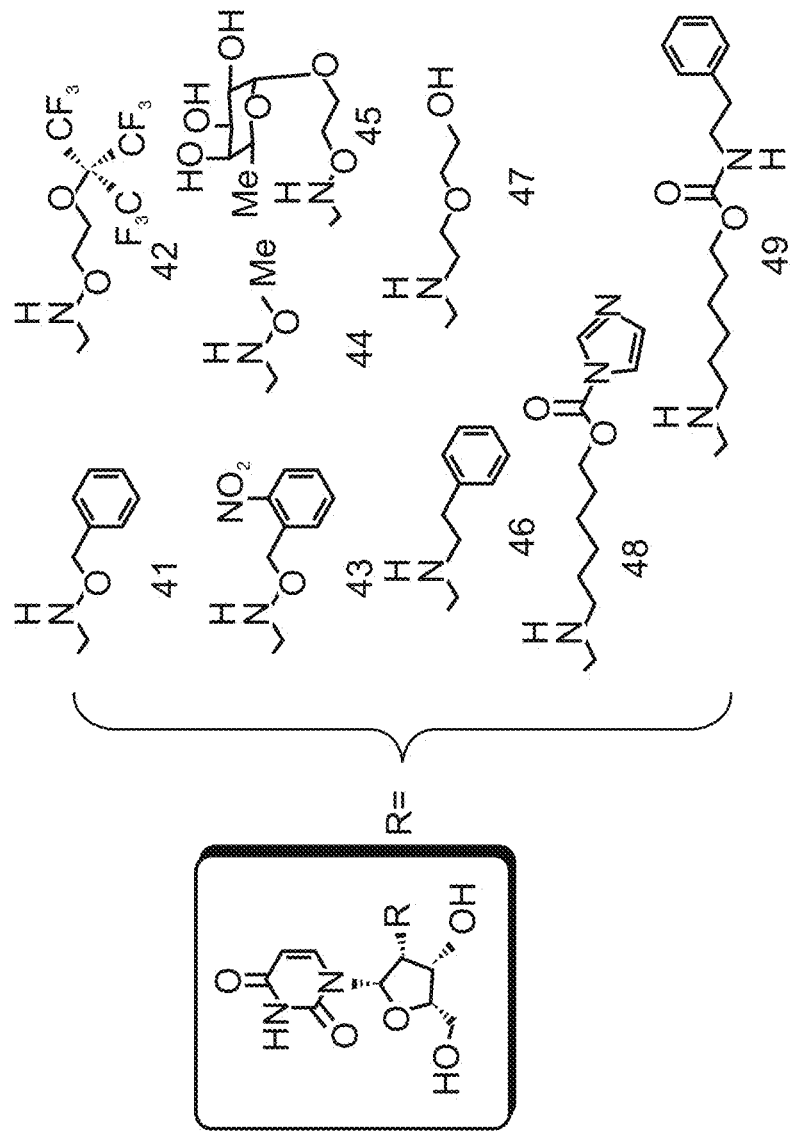

FIGS. 1a-c are schematic illustrations adapted from Eaton (1997) Curr. Opin. Chem. Biol. 1:10-16 depicting nucleic acid modifications, which can be incorporated in the nucleic acid molecules of the present invention. FIG. 1a shows 2'-deoxyuridines and uridines modified at position 5. FIG. 1b shows 2'-deoxyadenines, adenines and guanosines modified at position 8. FIG. 1c shows 2'-modified uridines.

Figure 2A:
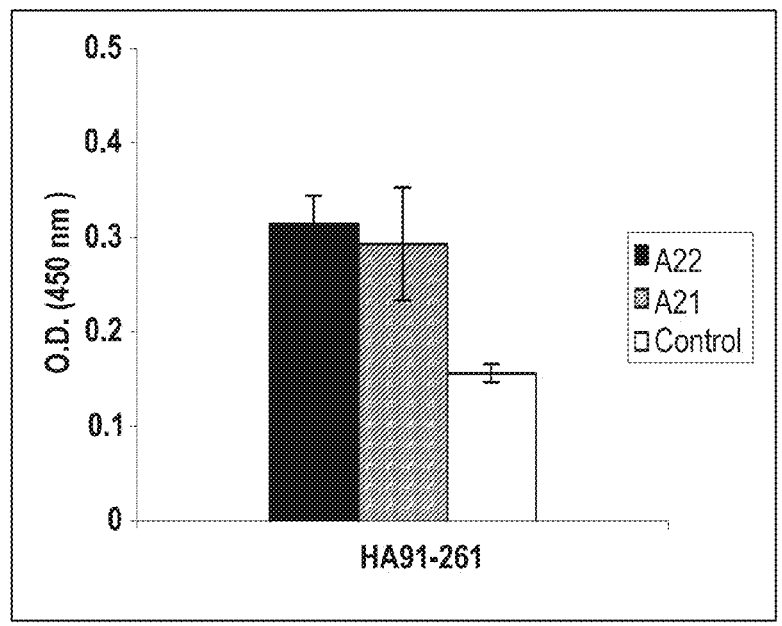
Figure 2B:
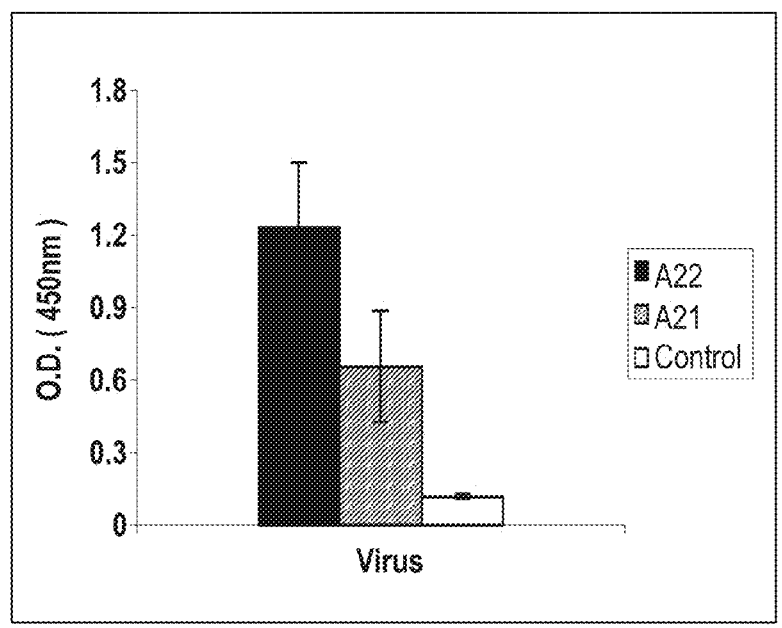

FIGS. 2a-b are histograms depicting binding levels of influenza specific aptamers generated according to the teachings of the present invention (A21 and A22) and control single stranded aptamer to an influenza intact virus or the $HA_{91-261}$ peptide as determined by ELISA. Note a significant binding of A21 and A22 to the viral peptide as compared to control nucleic acid is notable (p=0.042 and p=0.0008, respectively), and a significant reduction in A21 binding to the intact virus as compared to the A22 aptamer (p=0.017).

FIGS. 2c-e are schematic illustrations of proposed secondary structures as generated by the DNAdraw software (18) of the A22 aptamer (FIG. 2b), the A21 aptamer (FIG. 2c) and control oligonucleotide coding for the NP147-158 (FIG. 2d).

Figure 3A:
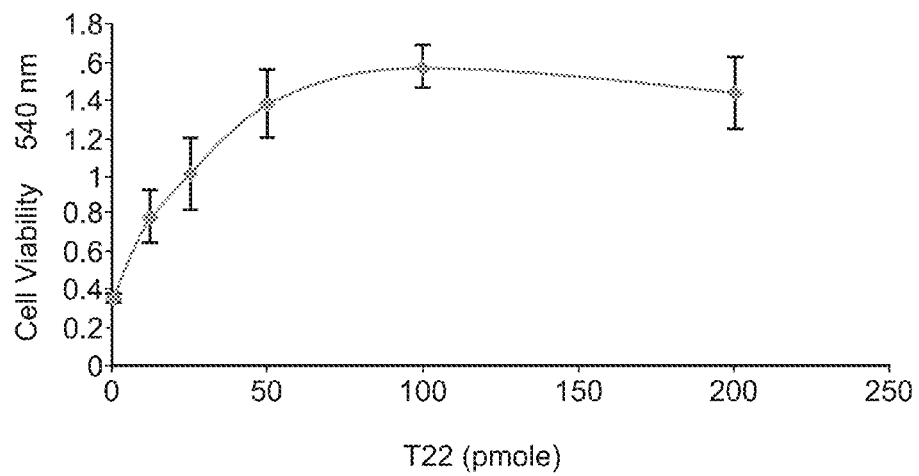

FIG. 3a is a dose response curve showing the effect of A22 aptamer of the present invention on viability of influenza virus treated MDCK cells as determined using the 3-(4,5-dimethylthiazol-2-yl)-2,5-diphenyltetrazolium bromide (MTT) assay. Note, the highest protective effect was achieved using A22 at the concentration range of 50 to 100 pmoles.

Figure 3B:
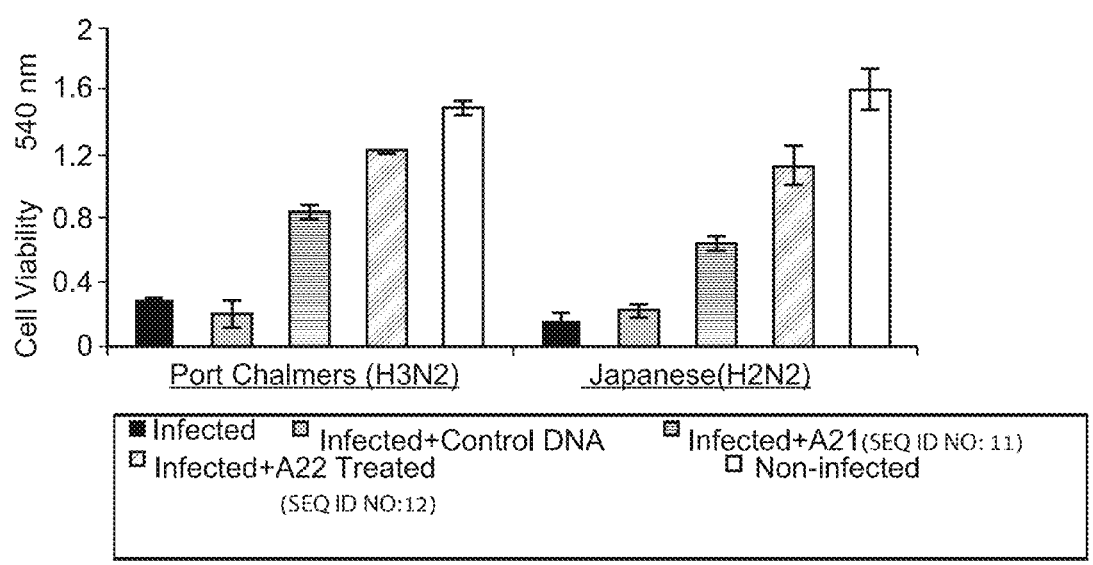

FIG. 3b is a histogram presentation depicting the protective effects of the A21 and A22 aptamers (each at 50 pmols) of the present invention on H3N2 and H2N2 infected MDCK cells.

Figure 3C:
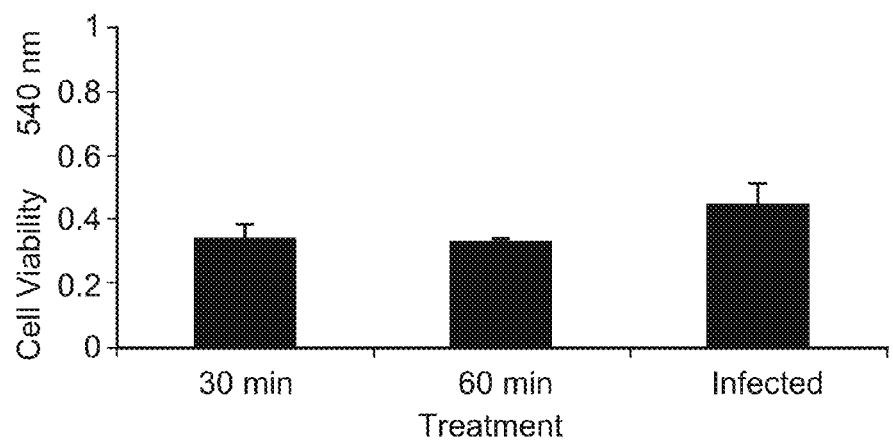

FIG. 3c is a histogram presentation illustrating a cell protective effect of A22 independent of the host cell proteins as determined by an MTT assay. MDCK cells were incubated with influenza virus 60 minutes following treatment for the indicated time periods with 50 pmole of A22. Note the insignificant difference between treated and control groups (p=0.237 for 30 minutes and p=0.09 for 60 minutes). Likewise, no significant difference in cell viability was evident between the two incubation times (p>0.05).

Figure 3D:
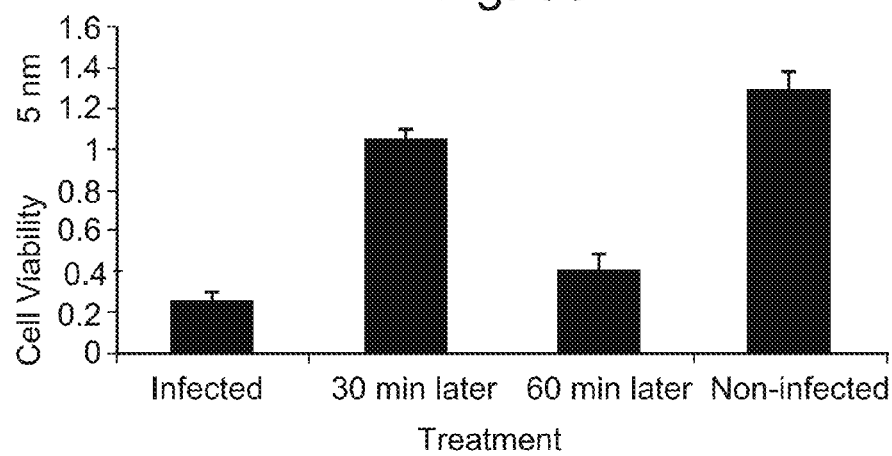

FIG. 3d is a histogram illustrating the protective effect of A22 on infected MDCK cells as determined by an MTT assay. MDCK cells were incubated with influenza virus for 30 min or 60 min prior to treatment with 50 pmole A22 for 60 min. Note that although an insignificant effect of A22 on 60 minutes virus treated MDCK cells was evident, a significant protective effect of A22 on 30 minutes virus treated MDCK cells was seen as compared to non-infected cells.

FIGS. 4a-f are photomicrographs depicting the effect of A22 on infection of cells with influenza. FIGS. 4a-c are light microscope images of MDCK cells following infection with influenza (FIG. 4a), following pre-treatment with A22 (FIG. 4b) or non-infected MDCK cells. FIGS. 4d-f are immunofluorescence images of MDCK cells following two days of incubation with influenza virus (FIG. 4d), influenza virus and A22 (FIG. 4e), or A22 alone (FIG. 4f).

Figures 5A, 5B, 5C:
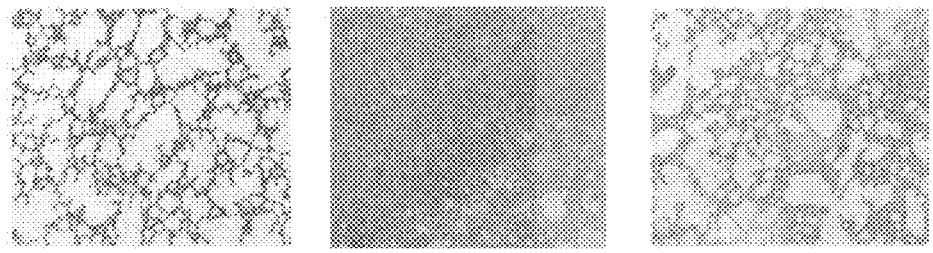
Figures 5D, 5E, 5F:
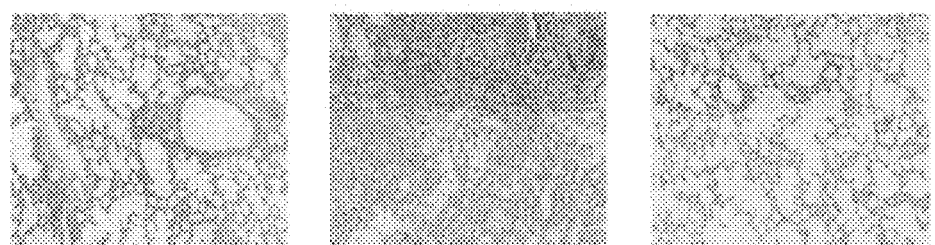

FIGS. 5a-f are photomicrographs showing lung sections of influenza virus infected BALB/c mice in the presence or absence of A22. Mice in the various treatment groups were sacrificed 6 days following intranasal inoculation with influenza virus and small portion of their lungs were removed and put into 10% neutralized formalin buffered for histological examinations. Staining was effected with Haematoxylin and eosin. FIG. 5a—Lung section from a non-infected mouse; FIG. 5b—Lung section from influenza virus infected mouse; FIG. 5c—Lung section from a mouse of group '−1 day', treated with A22 aptamer 1 day prior to viral infection; FIG. 5d—Mouse lung section of group '0 day' treated with A22 concomitantly with viral infection; FIGS. 5e-f—are two different sections from a lung of '+2 day' group treated with A22 two days following the infection. It is estimated that about 60% of the lung of that mouse corresponded to the pattern in FIG. 5f, which is similar to the histology of the non-infected control, whereas 40% of the lung contained bulk expansion of mononuclear cells (FIG. 5e).

Figure 6A:
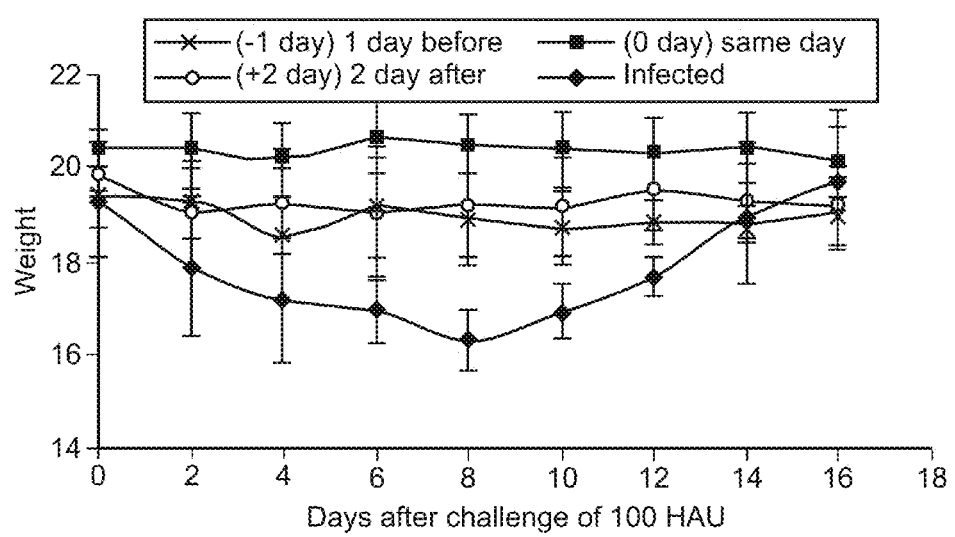
Figure 6B:
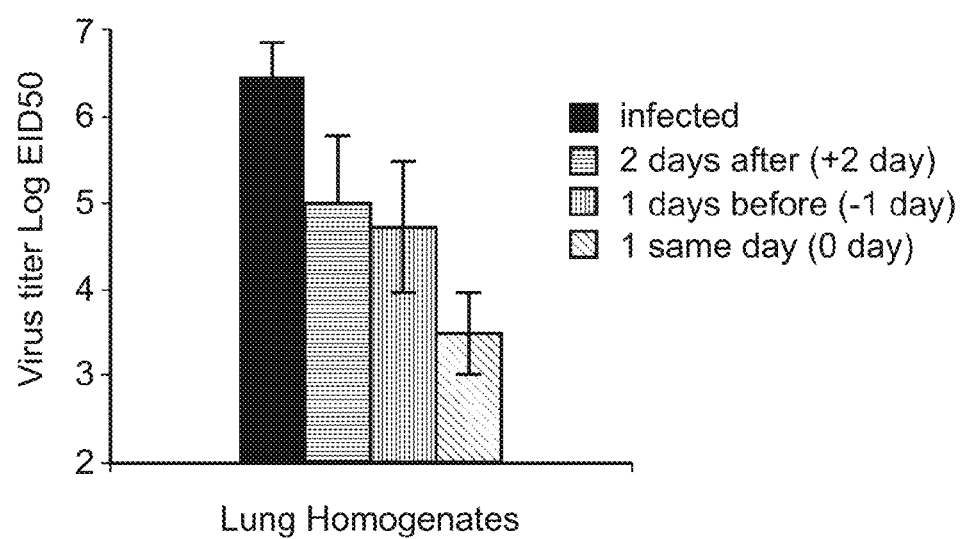

FIGS. 6a-b are graphs illustrating the protective effect of A22 on influenza virus infected mice as determined by body weight (FIG. 6a) and lung viral load (FIG. 6b). Mice were infected with 100 HAU A/Port Chalmers/1/73 by intranasal inoculation. −1 day group—mice treated with 2.5 nmole A22 one day prior to viral inoculation. +2 day group—mice treated with 2.5 nmole A22 two day following viral inoculation. '0 day group—mice treated with A22 concomitantly with viral inoculation. Body weight of infected but untreated mice was compared to the weight of mice treated with A22 for the time intervals (FIG. 6a). Alternatively, protection capacity of A22 was investigated by measuring viral load of lungs (FIG. 6b).

Figure 7A:
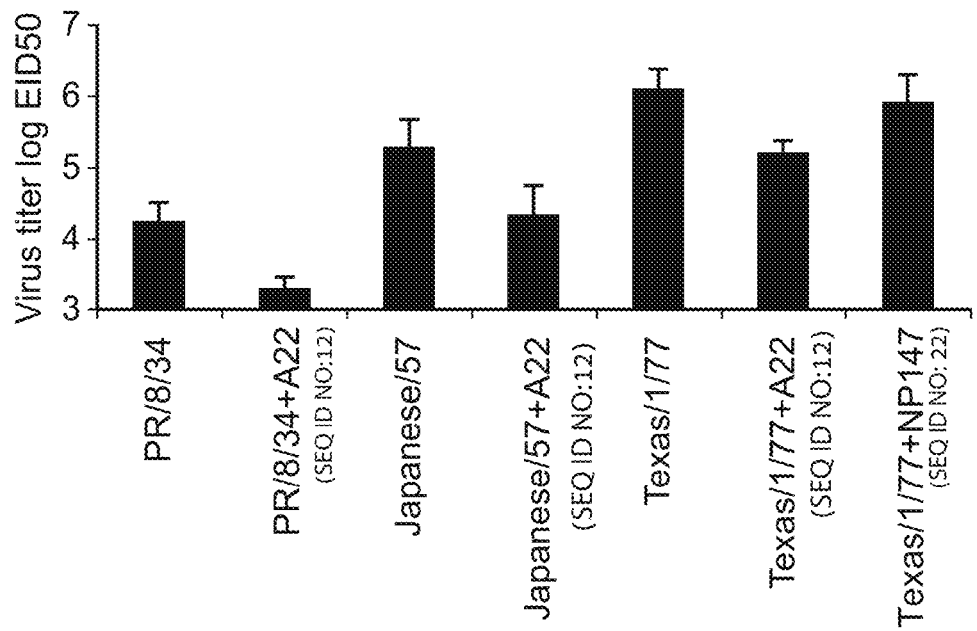

FIG. 7a is a graph depicting inhibition of mouse infection with several strains of influenza (each at 10 HAU) using the A22 aptamer.

Figure 7B:
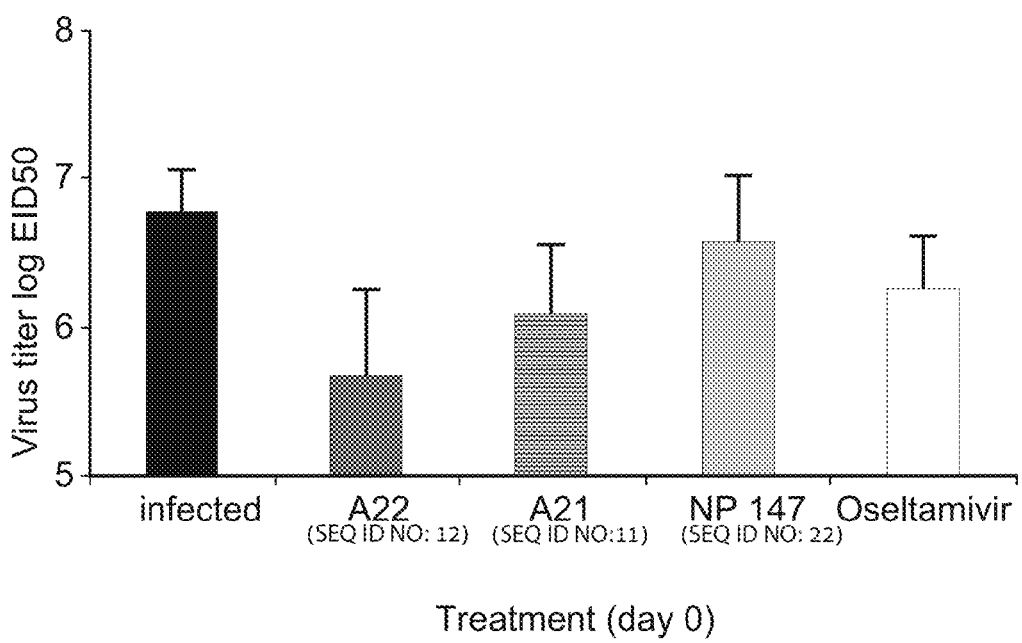
Figure 8A:
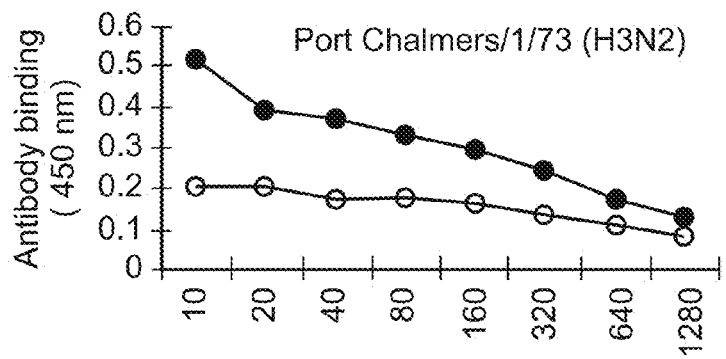
Figure 8B:
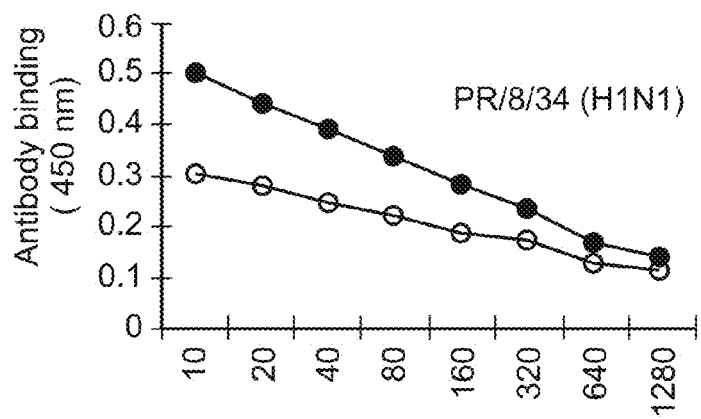
Figure 8C:
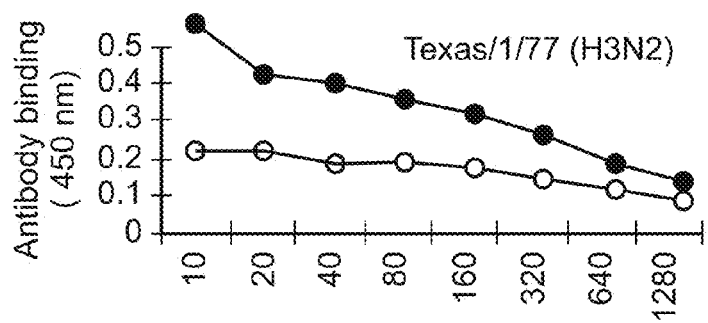
Figure 8D:
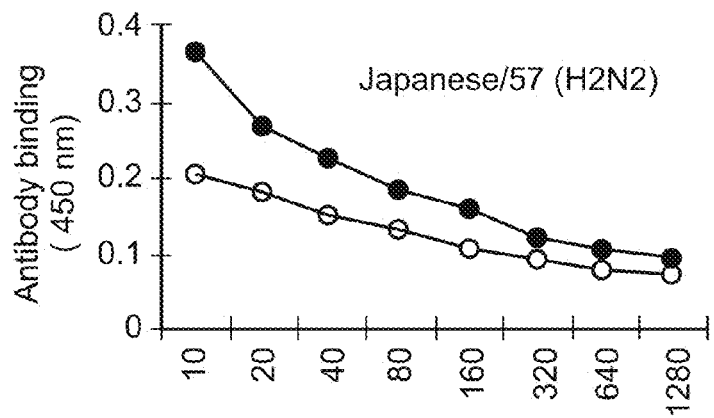
Figure 8E:
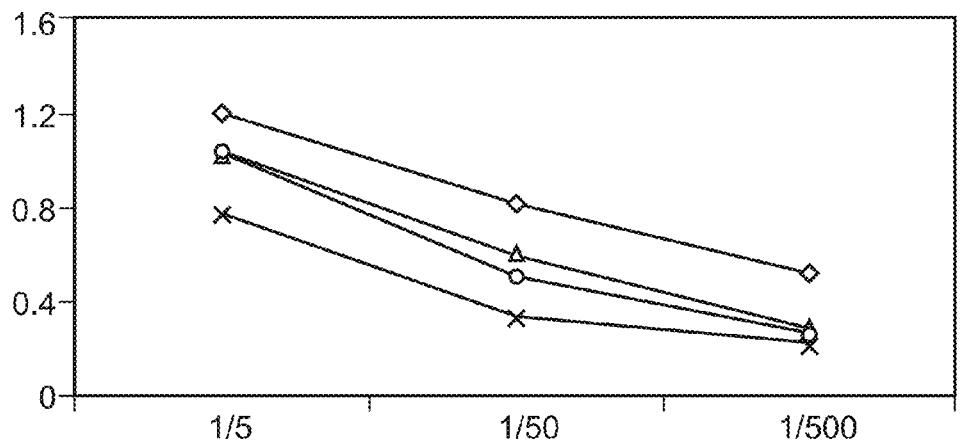

FIG. 7b is a graph depicting inhibition of mouse infection with the A/Texas/1/77 influenza strain using the A21 and A22 aptamers of the present invention, as well as control oligonucleotide and the anti-influenza drug Oseltamivir FIGS. 8a-d are graphs illustrating the cross-reactive effect of antibodies against the recombinant $HA_{91-261}$ fragment with a variety influenza virus strains as determined by ELISA. The IgG levels were measured by ELISA in serum samples of immunized (closed symbols) and non-immunized (opened symbols) mice. FIG. 8a—Port Chalmeras/1/73 infected mice; FIG. 8b—PR/8/34 infected mice; FIG. 8c—Texas/1/77 infected mice; FIG. 8d—Japanese/57 infected mice; and FIG. 8e illustrates strain-specific immune response induced by the intact A/Texas/1/77 (diamonds), A/Port Chalmers/1/73 (triangles)/A/PR/8/34 (circles) and A/Japanese/57 (crosses) viruses.

Figure 9A:
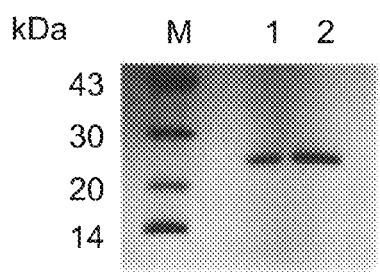

FIG. 9a is a photomicrograph depicting an SDS-PAGE analysis of $HA_{91-108}$ peptide purified by Ni-NTA column M—molecular weight marker; 1-10 μg of $HA_{91-108}$ peptide; 2-20 μg of $HA_{91-108}$ peptide.

Figure 9B:
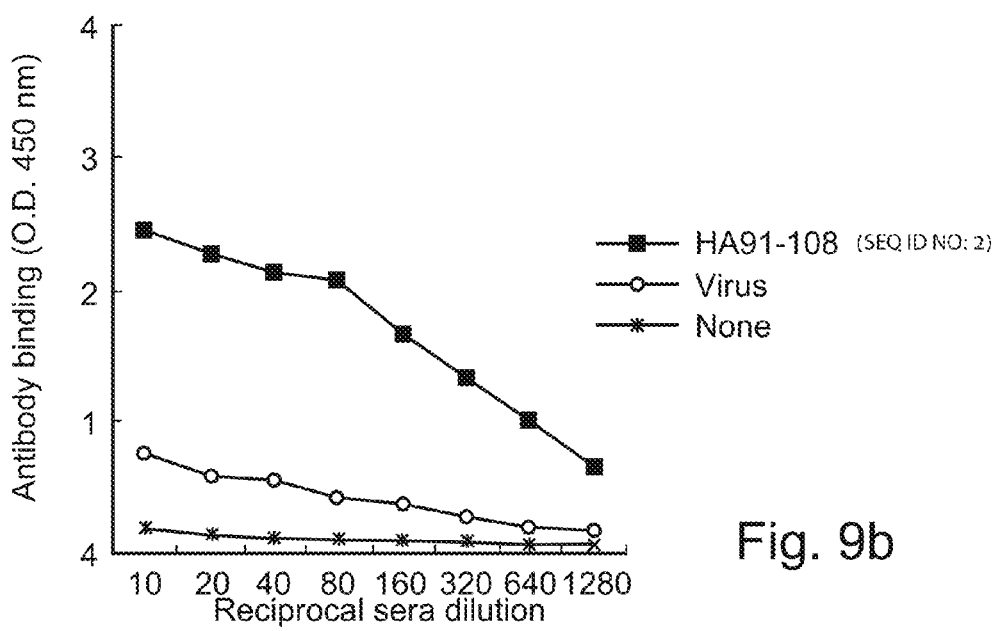

FIG. 9b is a graph depicting antigenisity of $HA_{91-108}$ peptide as determined by an ELISA assay. $HA_{91-261}$ peptide was coated to an ELISA plate and reacted with rabbit antiserum against $HA_{91-108}$ peptide (closed squares) or against the intact A/Texas/77 influenza virus (open circles). Control free antiserum is indicated by cross symbols.

FIGS. 10a-b are graphic representations depicting the immunogenecity of $HA_{91-261}$ peptide of the present invention as determined by an ELISA assay. Indicated sera dilutions from mice immunized with an $HA_{91-261}$ peptide either intranasally (tiangles) or in the foot pad (diamonds) or with a DNA vaccine (closed circles) corresponding to the peptide were contacted with microtiter plates coated with the $HA_{91-261}$ peptide (FIG. 10a) or the intact virus (FIG. 10b) and ELISA assay was effected. Sera from mice immunized by DNA priming-protein boosting is indicated by closed squares and from nonimmunized mice is indicated by cross symbols. Serum from mice immunized with control empty vector pCDNA3.1 is indicated with opened circles.

FIG. 10c is a histogram depicting the cross reactivity of anti $HA_{91-261}$ peptide with multiple influenza virus strains.

FIGS. 11a-b are graphs illustrating the production of IgA antibodies reactive with the $HA_{91-261}$ peptide of the present invention (FIG. 11a) or A/Texas/77 virus (FIG. 11b), following intranasal immunization of mice with $HA_{91-261}$ peptide (closed triangles) or DNA vaccine (closed squares) as determined by ELISA assay of lung homogenates. Combined DNA priming-protein fragment boosting is indicated by closed squares and non immunized control mice are indicated by cross symbols. Controls immunized with the vector pCDNA3.1 are indicated by opened squares.

Figures 12A, 12B:
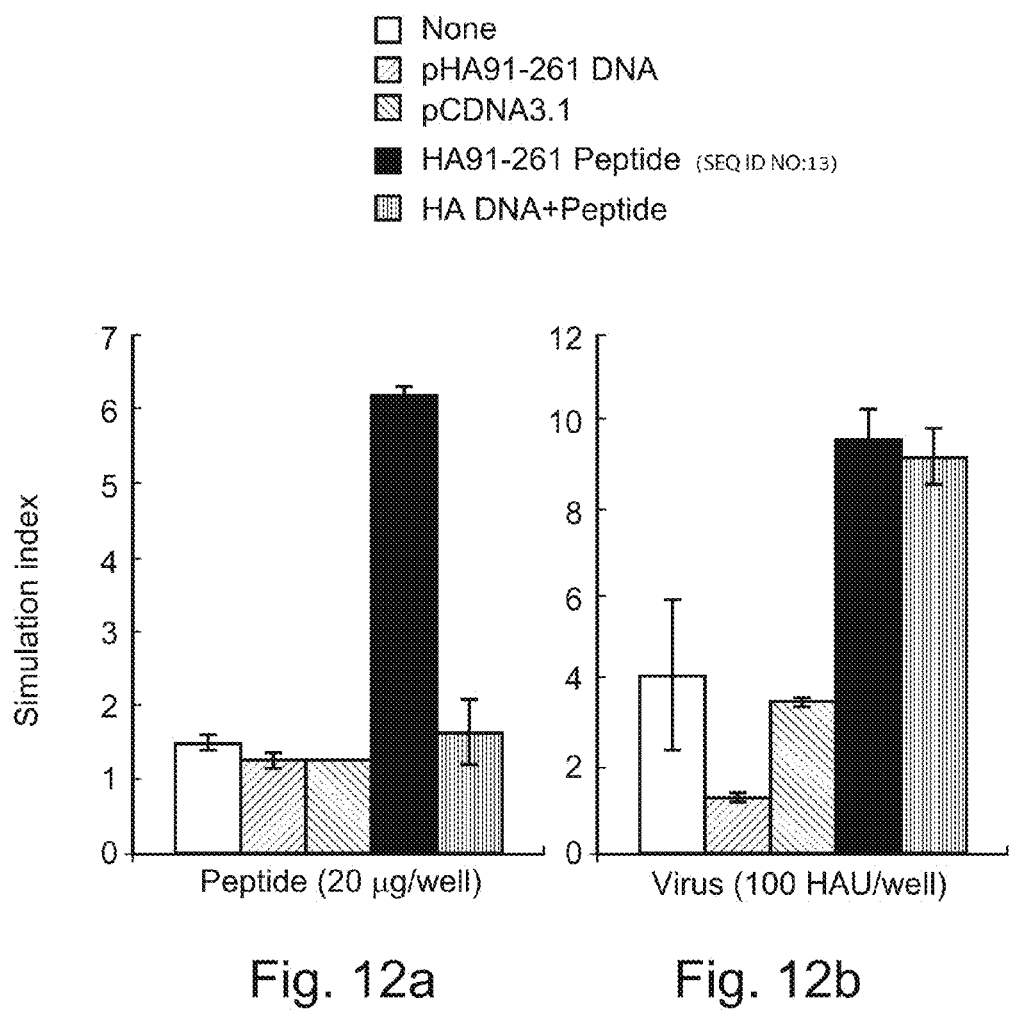

FIGS. 12a-b are histograms depicting proliferation of spleen cells from mice primed with $HA_{91-261}$ DNA and/or peptide in response to in vitro stimulation with $HA_{91-261}$ peptide (FIG. 12a) or viral particles (FIG. 12b). The proliferation was monitored by thymidine uptake and represented as stimulation index compared to media control.

Figures 13A, 13B:
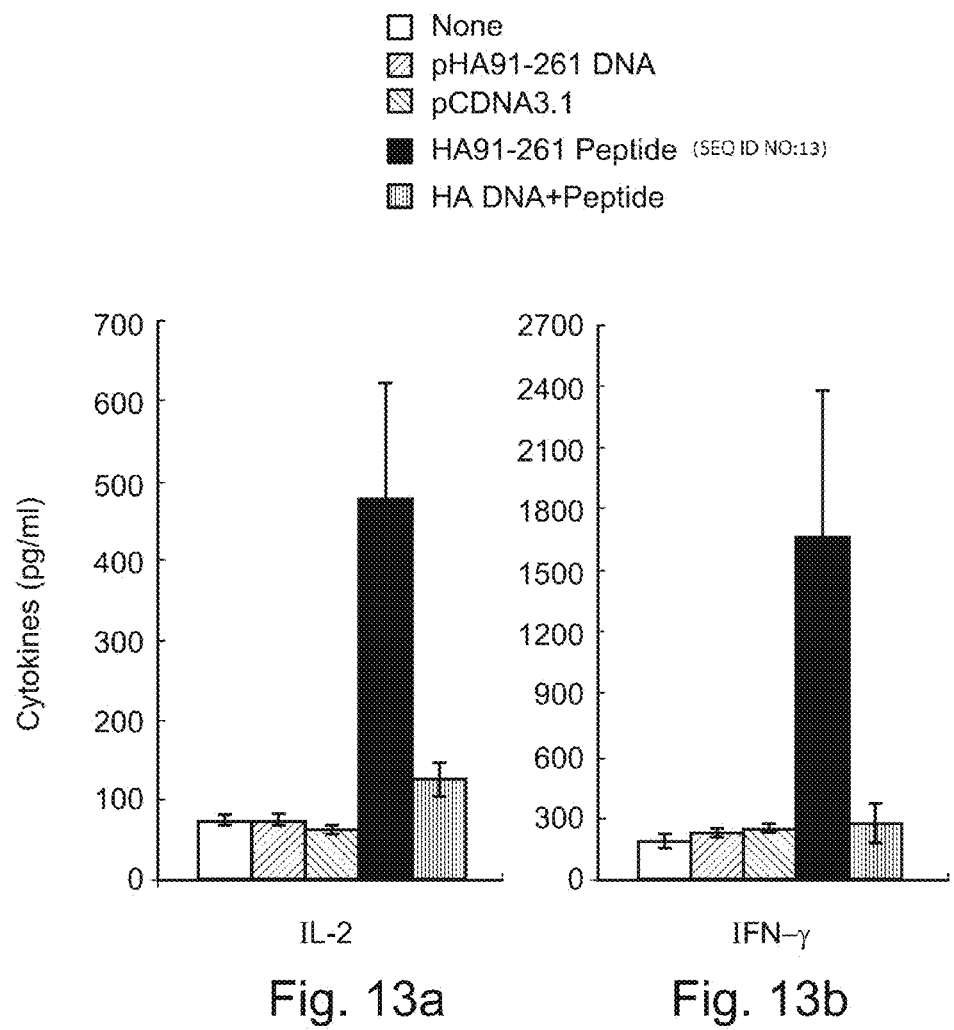

FIGS. 13a-b are histograms depicting cytokine secretion by spleen cells in response to influenza virus stimulation. Mice were immunized three times at 3-week intervals and retrieved spleen cells thereof were stimulated in vitro with inactivated influenza virus. Mean cytokine concentrations quantitated by comparison with a standard curve of purified cytokines are presented.

Figures 14A, 14B:
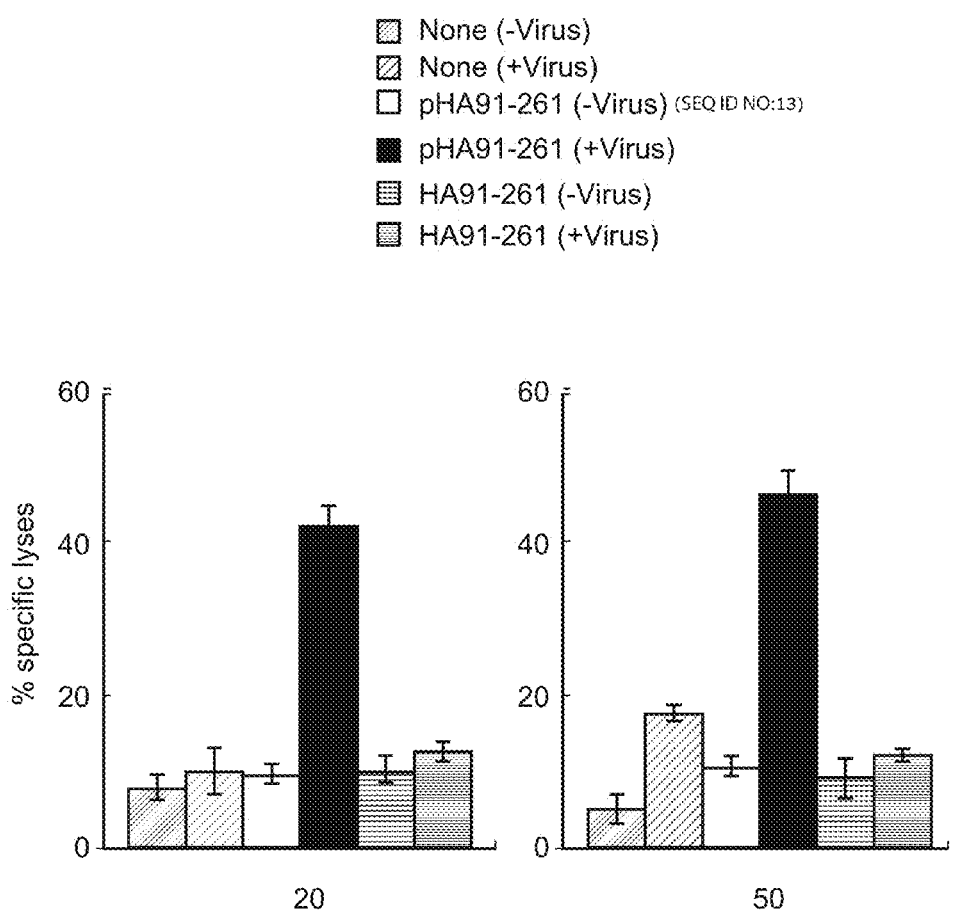

FIGS. 14a-b are histograms depicting CTL response in mice immunized with the peptide and/or DNA vaccines of the present invention. BALB/c mice were immunized with $pHA_{91-261}$ DNA or peptide and splenocytes were assayed for virus-specific CTL activity. Data for each group is depicted by lysis of $^{51}Cr$ labeled target cells at 20:1 (FIG. 14a) and 50:1 (FIG. 14b) effector to target ratio.

Figures 15A, 15B:
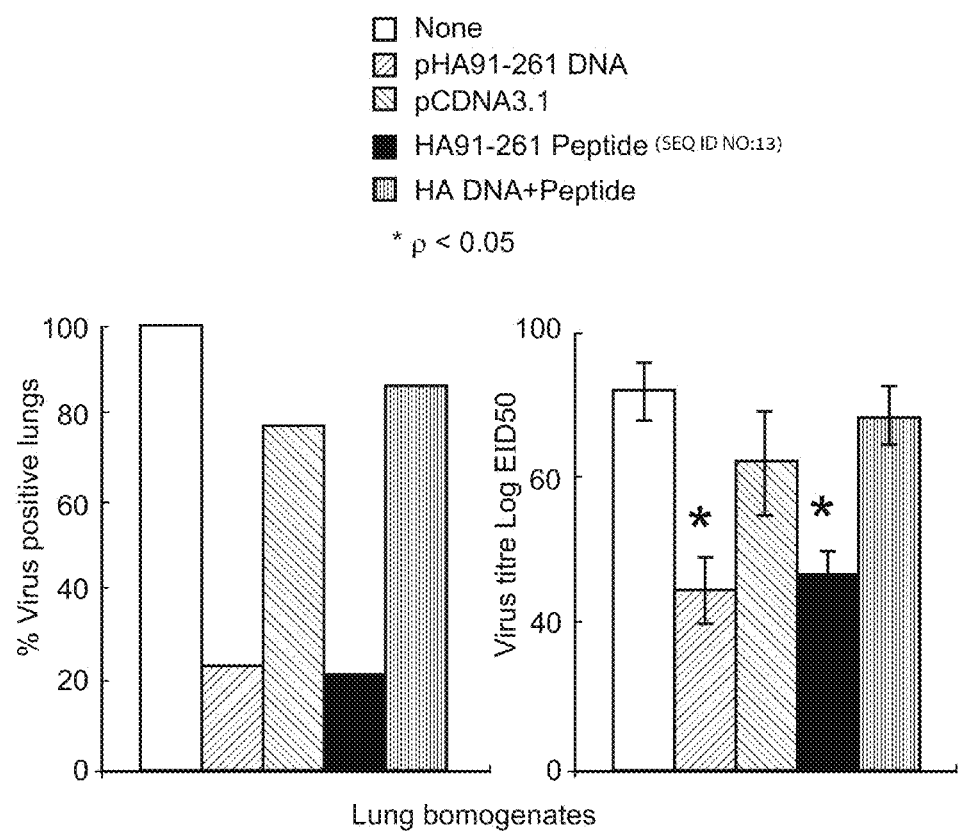

FIGS. 15a-b are histograms depicting protection against sublethal influenza virus challenge infection of mice immunized with $pHA_{91-261}$ DNA or peptide construct of the present invention. The mice were challenged 4 weeks following the last immunization, and sacrificed 5 days later. A $10^{-8}$ dilution of lung homogenate from each group was assayed for virus presence by a haemagglutination assay. The results are presented as percent virus positive lungs in each group at a $10^{-8}$ homogenates dilution (FIG. 15a), as well as $LogEID_{50}$ (FIG. 15b). An asterisk indicates a statistical significant difference ($p<0.05$).

DESCRIPTION OF THE PREFERRED EMBODIMENTS

The present invention is of nucleic acid molecules, polynucleotides, polypeptides, antibodies, and pharmaceutical compositions, which can be used for treating and detecting influenza virus infection in vertebrates such as avian, swines and humans.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Influenza is a major public health problem causing clinical morbidity, mortality and major economic losses each year of epidemic. To date, vaccination strategies, which constitute the basis of influenza control, have been directed at preventing morbidity and mortality in high-risk population groups. However, due to the rapid and unpredictable change of surface proteins (i.e., hemagglutinin and neuraminidase) of the influenza virus, which lead to the emergence of new viral strains, the development of an effective vaccine is complex and expensive.

Currently available antiviral drugs include the viral M2 ion channel blockers amantidine and rimantadine and the neuraminidase blockers zanamivir (Relenza™) and oseltamivir (Tamiflu™), which prevent release and budding of the virus particles. While the M2 ion channel blockers are ineffective against the type B influenza virus which does not encode the M2 protein and limited by severe side effects and acquired resistance, the use of zanamivir is associated with airway resistance and the use oseltamivir is highly priced.

As described hereinabove, the influenza virus encodes two surface antigens [neuraminidase and hemagglutinin (HA)], which undergo gradual changes (i.e., antigenic shifts and drifts), leading to the high antigenic variations in influenza. The HA molecule (75-80 kD, GenBank Accession No. AF092062, SEQ ID NO: 1) is the most significant antigen in defining the serological specificity of the different virus strains including a plurality of antigenic determinants, several of which are in regions that undergo sequence changes in different strains (i.e., strain-specific determinants) and others in regions which are common to many HA molecules (i.e., common determinants).

While reducing the present invention to practice, the present inventors have uncovered that oligonucleotides (e.g., aptamers) designed to bind conserved sequences in the HA polypeptide can be utilized to prevent virus binding to host cells. As is illustrated hereinunder and in the examples section, which follows, the present inventors, through laborious experimentation, have provided, for the first time, aptamer nucleic acid molecules, which can be used to diagnose and treat influenza virus infection. Such aptamer molecules exhibit viral cross-reactivity and as such can be used as universal vaccines against the influenza virus.

Aptamers are nucleic acid sequences of tertiary structures, which are selected to specifically bind a polypeptide of interest and inhibit a specified function thereof. Further description of aptamers and mechanism of action thereof is provided by Osborne, et al., Curr. Opin. Chem. Biol. 1997, 1(1): 5-9; and Patel, D. J., Curr. Opin. Chem. Biol. June. 1997; 1(1):32-46).

Thus, according to one aspect of the present invention there is provided a nucleic acid molecule including a polynucleotide sequence which is capable of specifically binding a polypeptide participating in influenza virus infection of cells.

The ability of the nucleic acid molecules of this aspect of the present invention to specifically bind a polypeptide which participates in influenza virus infection of cells allows the use thereof in influenza virus infection therapy and diagnostics.

As used herein "a polypeptide which participates in influenza virus infection of cells" refers to a polypeptide which is encoded by an orthomyxoviridea virus including type A-C influenza virus strains, a host cell polypeptide or a peptide fragment thereof.

Examples of influenza virus polypeptides which participate in virus infection of cells include but are not limited to hemagglutinin, neuraminidase, RNA-directed RNA polymerase core proteins including PB1, PB2 and PA, M1 and M2 matrix proteins, and NS proteins.

Examples of host cell polypeptides which participate in influenza virus infection include but are not limited to mucoproteins containing terminal N-acetyl neuraminic acid (NANA=sialic acid) groups, HLA proteins and endocytic proteins sialic acid containing glycans and mucosal glycoproteins.

It will be appreciated that polypeptide targets of this aspect of the present invention are preferably viral, to maximize specificity of the nucleic acid molecules of the present invention and reduce cytotoxicity thereof. Accordingly, preferred polypeptide target sequences include conserved amino acid sequences, which are shared by type A-C influenza viruses. Nucleic acid molecules generated to bind such sequences can be used as universal vaccines.

Examples of conserved viral peptide targets are provided in Table 1, below.

TABLE 1

Viral peptide targets

| Influenza virus protein (amino acid coordinates) | Peptide sequence | SEQ ID NO: | Reference |
|---|---|---|---|
| HA (91-108) | Ser-Lys-Ala-Phe-Ser-Asn-Cys-Tyr-Pro-Tyr-Asp-Val-Pro-Asp-Tyr-Ala-Ser-Leu | 2 | U.S. Pat. No. 4,474,757 |
| HA (306-318) | Pro-lys-tyr-val-lys-gln-asn-thr-leu-lys-leu-ala-thr | 3 | Rothbard (1998) Cell 52(4):515-23 |
| HA (305-323) | Cys-Pro-Lys-Tyr-Val-Lys-Gln-Asn-Thr-Leu-Lys-Leu-Ala-Thr-Gly-Met-Arg-Asn-Val | 4 | Rothbard (1998) Cell 52(4):515-23 |
| NP (335-350) | Ser-Ala-Ala-Phe-Glu-Asp-Leu-Arg-Val-Leu-Ser-Phe-Ile-Arg-Gly-Tyr | 5 | Dyer and Middleton Histocompatability testing, a practical approach Ed. Rickwood and Hames IRL Press Oxford (1993); Gulukota (1996) Biomolecular Engineering 13:81. |

TABLE 1-continued

Viral peptide targets

| Influenza virus protein (amino acid coordinates) | Peptide sequence | SEQ ID NO: | Reference |
|---|---|---|---|
| NP (380-393) | Glu-Leu-Arg-Ser-Arg-Tyr-Trp-Ala-Ile-Arg-Thr-Arg-Ser-Gly | 6 | Dyer and Middleton Histocompatability testing, a practical approach Ed. Rickwood and Hames IRL Press Oxford (1993); Gulukota (1996) Biomolecular Engineering 13:81. |
| M1 (220-236) | Gly-Thr-His-Pro-Ser-Ser-Ser-Ala-Gly-Leu-Lys-Asn-Asp-Leu-Leu-Glu-Asn | 7 | U.S. Pat. No. 5243030 |
| M1 (79-104) | Phe-Val-Gln-Asn-Ala-Leu-Asn-Gly-Asn-Gly-Asp-Pro-Asn-Asn-Met-Asp-Arg-Ala-Val-Lys-Leu-Tyr-Arg-Lys-Leu-Lys | 8 | U.S. Pat. No. 5243030 |
| M1 (64-80) | Phe-Thr-Leu-Thr-Val-Pro-Ser-Glu-Arg-Gly-Leu-Gln-Arg-Arg-Arg-Phe-Val | 9 | U.S. Pat. No. 5243030 |
| M1 (149-169) | Ala-Thr-Cys-Glu-Gln-Ile-ala-Asp-Ser-Gln-His-Arg-Ser-His-Arg-Gln-Met-Val-ala-Thr-Thr | 10 | U.S. Pat. No. 5243030 |

The nucleic acid molecules of this aspect of the present invention refer to single stranded or double stranded DNA or RNA molecules or any modifications thereof, which are capable of specifically binding the polypeptide-targets described hereinabove. The nucleic acid molecules of this aspect of the present invention are interchangeably referred to as "aptamers".

Typically, the nucleic acid molecules according to this aspect of the present are of varying length, such as 10-100 bases. It will be appreciated, though, that short nucleic acid molecules (e.g., 10-35 bases) are preferably used for economical, manufacturing and therapeutic considerations, such as bioavailability (i.e., resistance to degradation and increased cellular uptake).

According to presently known embodiments of this aspect of the present invention, the nucleic acid molecules are preferably those set forth in SEQ ID NOs. 11 and 12 (i.e., A21 and A22).

As mentioned hereinabove, the nucleic acid molecules of this aspect of the present invention are preferably modified to obtain enhanced bioavailability and improved efficacy to the target polypeptide. Modifications include but are not limited to chemical groups which incorporate additional charge, polarizability, hydrogen bonding, electrostatic interaction and fluxionality to the nucleic acid bases or to the entire molecule. Added or modified chemical groups are selected to include conformationally flexible linkages, which conform to the topology of the polypeptide target. Additionally, measures are taken that the chemistry for the modification of the nucleic acid molecules of this aspect of the present invention allows for either trisphosphate (NTP) or phosphoramidite synthesis.

Thus, for example, nucleic acid molecules of this aspect of the present invention preferably include modifications which allow specific cross-linking to the target polypeptide to thereby form high affinity compounds.

Appended cross-linking groups can contain hydrophobic, hydrophilic or charged functionality. Cross-linking may be accomplished by the formation of imine, acetal, ester and disulfide linkages as well as by conjugate addition to α,β-unsaturated carbonyl linkers. Examples of 2'-deoxyuridine nucleosides which are suitable for phosphoramidite synthesis are shown in FIG. 1a including small hydrophobic functional groups such as vinyl (group 1, FIG. 1a), large hydrophobic functional groups such as pyrenyl (groups 13-14, FIG. 1a) and carbonyl compounds with varying degrees of side chain hydrophobicity (groups 3, 6-11, FIG. 1a).

Pyrimidine base modifications, such as RNA uridine nucleoside modifications at position 5, can include hydrophobic groups which can be conjugated in the form of ketones [groups 17, 18 FIG. 1a, Crouch (1994) Nucleosides Nucleotides 13:939-944], amides [groups, 24, 27, FIG. 1a, Dewey (1995) J. Am. Chem. Soc. 117:8474-8475] and the like, which can be attached to either DNA or RNA nucleic acid molecules. It will be appreciated that amides can impart hydrogen bonding capabilities to the aptamer. In any case, as described hereinabove, cross-linking carbonyl groups can be attached to the 5-position of uridine (groups 15-18, FIG. 1a). It will be appreciated, though, that the expected reactivity of carbonyl linkers can differ significantly depending on the interface of the target polypeptide.

Examples of purine modifications are shown in FIG. 1b. For example hydrophobic substituents can be attached at the 8-position of RNA or DNA purine nucleosides (groups 28-30, FIG. 1b). The degree of steric hindrance can be varied via amide linkages (groups 31, 33, 34, 37 and 38, FIG. 1b). Hydrophylic (group 35, FIG. 1b) and charged (groups 36 and 39, FIG. 1b) groups may be appended to the 8 position of purine nucleosides. It will be appreciated that functional groups with known affinity to the target polypeptide can be attached to the 8 position of the purine base, such as a biotinylated nucleoside (group 40, FIG. 1b).

Additional sites for modifications include but are not limited to the 2'-position of RNA and the phosphodiester oxygens of RNA and DNA. A 2'-position pyrimidine nucleoside modification can be effected according to Sebesta (1996) Tetrahedron 52:14385-14402; McGee (1996) Tetrahedron Lett. 37:1995-1998; McGee (1996) J. Org. Chem. 61:781-785. Essentially, amine linkers, such as hydroxyl amine linkers can be used to attach hydrophobic groups with different topologies (groups 41-43, 46 and 49, FIG. 1c), hydrophilic groups (45 and 47, FIG. 1c) and groups exhibiting specific affinity to the target polypeptide (group 45, FIG. 1c).

As mentioned hereinabove, the nucleic acid molecules of this aspect of the present invention can also be modified to increase bioavailability thereof. The following illustrates non-limiting examples for such modifications.

The nucleic acid molecules of this aspect of the present invention may comprise heterocylic nucleosides consisting of purines and the pyrimidines bases, bonded in a 3' to 5' phosphodiester linkage.

Preferably used nucleic acid molecules are those modified in either backbone, internucleoside linkages or bases, as is broadly described hereinunder. Such modifications can oftentimes facilitate oligonucleotide uptake and resistance to intracellular conditions.

Array of synthetic chemistry is available for modification of nucleosides which may be converted to either NTPs or phosphoramidite reagents. For further details see Eaton and Pieken (1995) Annu. Rev. Biochem. 64:837-863.

Specific examples of nucleic acid molecules useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified nucleic acid backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623, 070; 5,663,312; 5,633,360; 5,677,437; and 5,677,439.

Other nucleic acid molecules which can be used according to the present invention, are those modified in both sugar and the internucleoside linkage, i.e., the backbone, of the nucleotide units are replaced with novel groups. The base units are maintained for complementation with the appropriate polynucleotide target. An example for such an nucleic acid sequence mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Nucleic acid molecules of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the nucleic acid molecules of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

As is illustrated in the Examples section, which follows, the present inventors have conclusively shown that the nucleic acid molecules of the present invention are capable of preventing influenza virus infection of cells in vitro and in vivo. Furthermore, the ability of the nucleic acid molecules of the present invention to inhibit viral spread following viral challenging, suggests the use of the nucleic acid molecules of the present invention in anti-influenza prophylactic and therapeutic applications.

Thus, according to another aspect of the present invention there is provided a method of treating influenza virus infection.

As used herein the term "treating" refers to preventing influenza virus infection or substantially reducing (i.e., alleviating or diminishing) symptoms associated with influenza virus infection.

The method is effected by providing to a subject in need thereof, a therapeutically effective amount of the nucleic acid molecule of the present invention described hereinabove.

As used herein "a subject in need thereof" refers to a subject suffering from influenza-virus associated symptoms or at risk of contracting influenza. Examples of such subjects include but are not limited to people aged 65 or over; people with chronic diseases of the heart, lung or kidneys, diabetes, immuno-suppression, or severe forms of anemia residents of nursing homes and other chronic-care facilities, children and teenagers taking aspirin therapy and who may therefore be at risk for developing reye syndrom reye syndrome after an influenza infection, and those in close or frequent contact with anyone at high risk.

Preferably, the nucleic acid molecules of the present invention are provided at a concentration of between, 0.1-150 μg/Kg body weight, preferably 1-100 μg/Kg body weight, more preferably 1-50 μg/Kg body weight and even more preferably 1-15 μg/Kg body weight.

The nucleic acid molecule (i.e., active ingredient) of the present invention can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Since activity of aptamers is directly correlated with a molecular weight thereof, measures are taken to conjugate the nucleic acid molecules of the present invention to high molecular weight carriers. Such high molecular weight carriers include, but are not limited to, polyalkylene glycol and polyethylene glycol (PEG), which are biocompatible polymers with a wide range of solubility in both organic and aqueous media (Mutter et al. (1979).

Alternatively, microparticles such as microcapsules or cationic lipids can serve as the pharmaceutically acceptable carriers of this aspect of the present invention.

As used herein, microparticles include liposomes, virosomes, microspheres and microcapsules formed of synthetic and/or natural polymers. Methods for making microcapsules and microspheres are known to the skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be generated by methods well known in the art such as those reported by Kim et al., Biochim Biophys. Acta, 728:339-348 (1983); Liu et al., Biochim Biophys. Acta, 1104:95-101 (1992); and Lee et al., Biochim. Biophys. Acta, 1103:185-197 (1992); Wang et al., Biochem., 28:9508-9514 (1989). Alternatively, the nucleic acid molecules of this aspect of the present invention can be incorporated within microparticles, or bound to the outside of the microparticles, either ionically or covalently.

Cationic liposomes or microcapsules are microparticles that are particularly useful for delivering negatively charged compounds such as the nucleic acid molecules of this aspect of the present invention, which can bind ionically to the positively charged outer surface of these liposomes. Various cationic liposomes are known to be very effective at delivering nucleic acids or nucleic acid-protein complexes to cells both in vitro and in vivo, as reported by Felgner et al., Proc. Natl. Acad. Sci. USA, 84:7413-7417 (1987); Felgner, Advanced Drug Delivery Reviews, 5:163-187 (1990); Clarenc et al., Anti-Cancer Drug Design, 8:81-94 (1993). Cationic liposomes or microcapsules can be generated using mixtures including one or more lipids containing a cationic side group in a sufficient quantity such that the liposomes or microcapsules formed from the mixture possess a net positive charge which will ionically bind negatively charged compounds. Examples of positively charged lipids which may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium ("DOTMA," see Felgner et al., Proc. Natl. Acad. Sci USA, 84:7413-7417 (1987); Felgner et al., Nature, 337:387-388 (1989); Felgner, Advanced Drug Delivery Reviews, 5:163-187 (1990)).

As mentioned hereinabove the pharmaceutical compositions of this aspect of the present invention may further include excipients. The term "excipient", refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the nucleic acid molecules of the present invention can also be expressed from a nucleic acid construct administered to the individual subject employing any suitable mode of administration, described hereinabove. Alternatively, the nucleic acid construct is introduced into a suitable cell via an appropriate delivery vehicle/method (transfection, transduction, and the like) and an expression system as needed and then the modified cells are expanded in culture and returned to the individual.

To enable cellular expression of RNA nucleic acid molecules of the present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. Preferred promoters for use in aptamer expression vectors include the pol III promoters such as the human small nuclear U6 gene promoter and tRNA gene promoters. The use of U6 gene transcription signals to produce short RNA molecules in vivo is described by Noonberg et al., Nucleic Acids Res. 22:2830-2836 (1994), and the use of tRNA transcription signals is described by Thompson et al., Nucleic Acids Res., 23:2259-2268 (1995).

It will be appreciated that many pol III promoters are internal and are located within the transcription unit such that pol III transcripts include promoter sequences. To be useful for expression of aptamer molecules, these promoter sequences should not interfere with the structure or function of the aptamer. Therefore a preferred RNA pol III RNA promoter is the U6 gene promoter which is not internal [Kunkel and Pederson, Nucleic Acids Res, 17:7371-7379 (1989); Kunkel et al., Proc. Natl. Acad Sci. USA 83:8575-8579 (1986); Reddy et al., J. Biol. Chem. 262:75-81 (1987)]. Suitable pol III promoter systems useful for expression of aptamer molecules are described by Hall et al., Cell 29:3-5 (1982), Nielsen et al., Nucleic Acids Res. 21:3631-3636 (1993), Fowlkes and Shenk, Cell 22:405-413 (1980), Gupta and Reddy, Nucleic Acids Res. 19:2073-2075 (1991), Kickhoefer et al., J. Biol. Chem. 268:7868-7873 (1993), and Romero and Blackburn, Cell 67:343-353 (1991). The use of pol III promoters for expression of RNA molecules is also described in WO 95/23225 by Ribozyme Pharmaceuticals, Inc.

Other promoters useful for expressing the aptamers of the present invention include, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus can be obtained as an SV40 restriction fragment which also contains the SV40 viral origin of replication [Fiers et al., Nature, 273: 113 (1978)]. The immediate early promoter of the human cytomegalovirus can be obtained as a HindIII E restriction fragment (Greenway, P. J. et al., Gene 18: 355-360 (1982)). It will be appreciated that promoters from the host cell or related species also can also be used.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer are described by Lasic D., Liposomes: From Physics to Applications, Elsevier: Amsterdam, 1993.

Preferably, cationic lipids are used in combination with a neutral lipid in equimolar amounts as described hereinabove. Neutral lipids of use in transfection complexes include, for example, dioleoyl phosphatidylethanolamine (DOPE), Hui et al., Biophys. J. (71)590-599 (1996); cholesterol, Liu et al., Nat. Biotech. 15:167-173 (1997).

Typically a lipid mixtures is prepared in chloroform, dried, and rehydrated in, e.g., 5% dextrose in water or a physiologic buffer to form liposomes. The resulting liposomes are mixed with a nucleic acid solution with constant agitation to form the cationic lipid-nucleic acid transfection complexes. Preferred transfection complex size for intravenous administration is from 50 to 5000 nm, most preferably from 100 to 400 nm.

It will be appreciated that DNA/lipid complexes are preferably prepared at a DNA concentration of about 0.625 mg/ml. The dose delivered is from about 10·mu·g to about 2 mg per gram of body weight. Repeat doses may be delivered at intervals of from about 2 days to about 2 months, The most preferred constructs for in-vivo use according to presently known embodimants are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof.

Preferred modes for in-vivo nucleic acid delivery protocols are provided in Somia and Verma (2000) Nature Reviews 1:91-99, Isner (2002) Myocardial gene therapy Nature 415: 234-239; High (2001) Gene therapy: a 2001 perspective. Haemophilia 7:23-27; and Hammond and McKirnan (2001) Angiogenic gene therapy for heart disease: a review of animal studies and clinical trials. 49:561-567.

Prior to, concomitant with or following providing the nucleic acid molecule of the present invention an agent can be provided to the subject.

An agent can be a molecule which facilitates prevention or treatment of influenza infection or clinical conditions associated with influenza infection such as pneumonia. Examples of agents, according to this aspect of the present invention include, but are not limited to, immunomodulatory agents (e.g., antibodies), antibiotics, antiviral agent (e.g., amantidine), antisense molecules, rybosymes and the like.

The antibody-like nature (i.e., specific binding to a polypeptide target) of the nucleic acid molecules of the present invention, allows the agents described hereinabove to be specifically targeted to an infectious tissue upon attachment to the administered nucleic acid molecule or to a lipid carrier containing same.

For example an antisense molecule directed at an anfluenza virus polypeptide (further described in the background section) can be targeted using the apatmeric sequences of the present invention. "Chimeric" antisense molecules", are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such include RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Alternatively a ribozyme sequence can be targeted using the nucleic acid molecules of the present invention. Ribozymes are being increasingly used for the sequence-specific inhibition of gene expression by the cleavage of mRNAs. Several ribozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a ribozyme designed to selectively destroy Hepatitis C Virus (HCV) RNA, (Ribozyme Pharmaceuticals, Incorporated—WEB home page).

Optionally, "DNAzymes" can be targeted using the methodology of the present invention [Breaker, R. R. and Joyce, G. Chemistry and Biology (1995); 2:655; Santoro, S. W. & Joyce, G. F. Proc. Natl, Acad. Sci. USA 1997; 943:4262]. DNAzymes are single-stranded, and cleave both RNA. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl. Acad. Sci. USA 199; for rev of DNAzymes see Khachigian, L M Curr Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

Methods of nucleic acid-lipid coupling are well known in the art and described in U.S. Pat. No. 5,756,291.

For example, Asseline, U. et al. [Proc Natl Acad Sci 81, 3297-3301 (1984)] describes the covalent linking of an intercalating agent via a polymethylene linker through a 3'-phosphate group. Mori, K. et al. (FEBS Letters 249:213-218 (1989)) describes the covalent attachment of groups via a methylene linker at the 5'-terminus of oligonucleotides. PCT application WO89/05853 published Jun. 29, 1989, the entire disclosure of which is hereby incorporated by reference, describes a variety of methods for formation of conjugates between nucleotide sequences and chelating agents; the chelating agent is joined to the nucleotides sequence by either a covalent bond or a linking unit derived from a polyvalent functional group.

Thus, the aptamers or modified aptamers of the invention may be used alone in therapeutic applications or may be used for targeting agents to deliver pharmaceuticals or toxins to desired targets.

The ability of the nucleic acid molecules of the present invention to specifically bind polypeptides of the influenza virus allows the use thereof in diagnostic applications.

To date, a number of tests are available for the diagnosis of influenza A and B. A traditional approach for identifying influenza viruses in biological samples involves cell culturing, thereby providing highly sensitive and specific detection of viral infection. However, this approach is significantly limited by the time required for cell culturing and identification of influenza virus can range between 2 and 10 days, thus making it ineffective in guiding the physician to an appropriate therapy. Since influenza virus infection is normally self-limited, diagnosis must be rapid if therapy is to be effective. Thus, cell culture methods are used only for providing retrospective epidemiological information.

Other influenza diagnostic methods include the use of monoclonal immunofluorescence assays [Spada, B. et al., J. Virol. Methods, (1991) 33: 305] and enzyme-linked immunoassay [EIA, Ryan-Poirier, K. A. et al., J. Clin. Microbiol., (1992) 30: 1072]. However, not only are these methods limited to the identification of type A influenza virus infection, but they require considerable technical expertise, and result in high levels of false-positive.

Thus, according to yet another aspect of the present invention there is provided a method of identifying influenza virus in a biological sample.

As used herein a biological sample refers to any body sample such as blood, spinal fluid, pleural fluid, respiratory fluids and nasal aspirates. Methods of obtaining body fluids from vertebrates are well known in the art. For example, a nasal wash can be obtained as described in Henrickson, J. Viol. Methods, 46:189-206, 1994 or Hall and Douglas, J. Infect. Dis., 131:1-5, 1975.

The method is effected by contacting the biological sample with a nucleic acid molecule including a polynucleotide sequence capable of specifically binding an influenza virus polypeptide, described hereinabove.

The nucleic acid molecules of the present invention can be attached to a solid substrate, such as described hereinbelow.

Contacting is effected under conditions which allow the formation of a polyepeptide-nucleic acid molecule duplex.

Duplexes are preferably washed to remove any non-specifically bound polypeptides allowing only those nucleic acid molecules specifically bound within the complexes to be detected.

Polypeptide-bound nucleic acid molecules in the biological sample are detected to thereby identify the influenza infection.

In general monitoring of polypeptide-nucleic acid molecule complexes is well known in the art and may be effected as described hereinabove. These approaches are generally based on the detection of a label or marker, such as described hereinbelow.

Preferably, detection of an infected sample is effected by comparison to a normal sample, which is not infected with an influenza virus.

To generate the nucleic acid molecules of the present invention, a robust selection approach is preferably employed.

Thus, according to an additional aspect of the present invention there is provided a method of generating a nucleic acid molecule, which is capable of inhibiting influenza virus infection of cells.

The method is effected as follows:

First, a plurality of nucleic acid molecules are contacted with a polypepitde target, which participates in influenza virus infection of cells as described hereinabove.

Following duplex formation (i.e., a non-Watson Crick complementation between the polypeptide target and the nucleic acid molecules), at least one nucleic acid molecule of the plurality of nucleic acid molecules which is capable of specifically binding the polypeptide is identified.

Finally, polypeptide bound nucleic acid molecules are isolated to thereby generate the molecule which is capable of inhibiting influenza virus infection.

Double stranded DNA molecules can be generated from a library of oligonucleotide sequences including a randomized polynucleotide sequence flanked by two defined nucleotide sequences which can be used for polymerase chain reaction to (PCR) primer binding. The library is amplified to yield double-stranded PCR products [Bielinska (1990) Science 250(4983):997-1000]. The randomized sequences can be completely randomized (i.e., the probability of finding a base at any position being 1:4) or partially randomized (i.e., the probability of finding a base at any position is selected at any level between 0-100%).

For preparation of single stranded aptamers, the down stream primer is biotinylated at the 5' end and PCR products are applied to an avidin agarose column. Single stranded DNA sequences are recovered by elution with e weakly basic buffer.

Single stranded RNA molecules can be generated from an oligonucleotide sequence library, which is amplified to yield double-stranded PCR products containing a T7 bacteriophage polymerase promoter site. RNA molecules can then be produced by in vitro transcription using T7 RNA polymerase.

The nucleic acid molecules of this aspect of the present invention can be generated from naturally-occurring nucleic acids or fragments thereof, chemically synthesized nucleic acids, enzymatically synthesized nucleic acids or nucleic acid molecules made by a combination of the foregoing techniques.

The library of this aspect of the present invention is generated sufficiently large to provide structural and chemical coverage of selected nucleic acid modifications described hereinabove.

Typically, a randomized nucleic acid sequence library according to this aspect of the present invention includes at least $10^{14}$ sequence variants.

Nucleic acid modifications can be effected prior to incubation with the target polypeptide. In this case, although screening is effected on the final modified aptamer, modification is restricted not to interfere with any process, such as an enzymatic process (e.g., transcription), which takes place during the screening.

Alternatively, a nucleic acid molecule can be modified following selection (i.e., isolation of a polypeptide bound nucleic acid molecule). Thus, a wide range of functional groups can be used simultaneously. In this case, electrospray ionization mass spectrometry (ESI-MS) can be used to elucidate the right functional group [Pomerantz (1996) Anal. Chem. 68:1989-1999].

In any case, once nucleic acid molecules are obtained they are contacted with the polypeptide target, as mentioned hereinabove.

Incubation of the nucleic acid molecules with the target polypeptide of this aspect of the present invention is preferably effected under physiological conditions. As used herein the phrase "physiological conditions" refers to salt concentration and ionic strength in an aqueous solution, which characterize fluids found in the metabolism of vertebrate animal subjects which can be infected with influenza virus, also referred to as physiological buffer or physiological saline. For example physiological fluids of human subjects are represented by an intracellular pH of 7.1 and salt concentrations (in mM) of sodium 3-15; potassium 140; magnesium 6.3; Calcium $10^{-4}$; Chloride 3-15, and an extracellular pH of 7.4 and salt concentrations (in mM) of sodium 145; potassium 3; Magnesium 1-2; Calcium 1-2; and Chloride 110.

The nucleic acid molecules can be incubated with the target polypeptide either in solution or when bound to a solid substrate.

It will be appreciated that some of the above-described base modifications can be used as intermediates for attaching the nucleic acid molecule to a solid substrate. For example, the modified uridine shown in group 48 of FIG. 1*c*, can serve as a common intermediate which may be further modified by substitution of the imidazole with a wide variety of hydrophobic, hydrophilic, charged and cross linking groups, prior to activation as the phosphoramidite reagent used in solid phase synthesis.

Methods for attaching nucleic acid molecules to solid substrates are known in the art including but not limited to glass-printing, described generally by Schena et al., 1995, Science 270:467-47, photolithographic techniques [Fodor et al. (1991) Science 251:767-773], inkjet printing, masking and the like.

Typically, a control sample is included to select against nucleic acid molecules which bind to non-target substances such as the solid support and/or non target epitopes.

Separation of unbound nucleic acid sequences and identification of bound nucleic acid sequences can be effected using methods well known in the art. Examples include, but are not limited to, selective elution, filtration, electrophoresis and the like (see U.S. Pat. No. 5,756,291).

Alternatively, bound aptameric molecules can be identified by imaging. For example, optical microscopy using bright field, epi-fluorescence or confocal methods, or scanning probe microscopy can be used to identify a polypeptide bound nucleic acid molecule (see U.S. Pat. No. 6,287,765). To facilitate visualization, nucleic acid molecules or polypeptides are preferably labeled using any radioactive, fluorescent, biological or enzymatic tags or labels of standard use in the art.

The following illustrates a number of labeling methods suitable for use in the present invention. For example, nucleic acid molecules of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, fluorescent moieties are used, including but not limited to fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif.]. Alternatively, a radioactive label is used [Zhao et al. (1995) Gene 156:207]. However, because of scattering of radioactive particles, and the consequent requirement for widely spaced binding sites, the use of fluorophores rather than radioisotopes is more preferred.

It will be appreciated that the intensity of signal produced in any of the detection methods described hereinabove may be analyzed manually or using a software application and hardware suited for such purposes.

Isolation of an aptamer sequence (i.e., polypeptide-bound nucleic acid) typically involves sequence amplification such as by PCR. Amplification may be conducted prior to, concomitant with or following separation from the target polypeptide. The PCR method is well known in the art and described in, e.g., U.S. Pat. Nos. 4,683,195 and 4,683,202, and 4,800,159 as well as Methods in Enzymology (1987) 155:335-350. It will be appreciated that if RNA molecules are used, the amplified DNA sequences are transcribed into RNA.

Other methods of amplification may be employed including standard cloning, ligase chain reaction and the like (see U.S. Pat. No. 4,957,858). For example, once an aptamer is identified, linkers may be attached to each side to facilitate cloning into standard vectors. Single stranded or double stranded aptamers, may be cloned and recovered.

The recovered nucleic acid molecule, in the original single-stranded or duplex form, can then be used for iterative rounds of selection and amplification (i.e., target polypeptide binding). Typically, following three to six rounds of selection/amplification, nucleic acid molecules which bind with a preferred affinity of nM to M range can be obtained.

It will be appreciated that methods for identifying nucleic acid molecules capable of specifically binding polypeptide targets are known in the art [e.g., U.S. Pat. No. 5,270,163, Ellington and Szostak (1990) Nature 346:818-822, Bock et al. (1992) Nature 255:564-566, Wang et al. (1993) Biochemistry 32:1899-1904, and Bielinska et al. (1990) Science 250: 997-1000]. For example, U.S. Pat. No. 5,270,163 discloses a method referred to as SELEX (Systematic Evolution of Ligands by Exponential Enrichment) for the identification of nucleic acid ligands as follows. A candidate mixture of single-stranded nucleic acids having regions of randomized sequence is contacted with a target compound and those nucleic acids having an increased affinity to the target are partitioned from the remainder of the candidate mixture. The partitioned nucleic acids are amplified to yield a ligand enriched mixture. Bock and co-workers describe a method for identifying oligomer sequences that specifically bind target biomolecules involving complexation of the support-bound target molecule with a mixture of oligonucleotides containing random sequences and sequences that can serve as primers for PCR [Bock et al. (1992) Nature 255:564-566]. The target-oligonucleotide complexes are then separated from the support and the uncomplexed oligonucleotides, and the complexed oligonucleotides are recovered and subsequently amplified using PCR. The recovered oligonucleotides may be sequenced and subjected to successive rounds of selection using complexation, separation, amplification and recovery.

Alternatively, the nucleic acid sequences of the present invention can be generated by rational drug design.

Rational drug design is a potent means of identifying enzyme inhibitors which, for example, has notably been used to identify HIV protease (Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109), and bcr-abl tyrosine kinase inhibitors (Mauro M J. et al., 2002. J Clin Oncol. 20, 325-34) used to provide the first effective pharmacological cures for human acquired immunodeficiency syndrome (AIDS) caused by human immunodeficiency virus (HIV)), and a human cancer (chronic myeloid leukemia), respectively.

To identify a putative aptamer sequence via rational drug design by screening a nucleic acid sequence structure database ("3D database"), software employing "scanner" type algorithms employ atomic coordinates defining the three-dimensional structure of a binding pocket of a molecule, such as the sialic acid receptor binding pocket of the infuenza hemagglutinin polypeptide (amino acid coordinates 116-261 of GenBank Accession No. AF092062), and of a nucleic acid sequence structure stored in the database to computationally model the "docking" of the screened aptamer structure with the binding pocket so as to qualify the binding of the binding pocket with the aptamer structure. Iterating this process with each of a plurality of putative aptamer structures stored in the database therefore enables computational screening of such a plurality to identify a chemical structure potentially having a desired binding interaction with the binding pocket, and hence the putative inhibitor.

Examples of nucleic acid structure databases for identifying the nucleic acid molecule of the present invention include the RNA structure database (wwwdotRNABasedotorg) and the NDB database (http://wwwdotimb-jenadotde/RNAdothtml#Databases).

Alternatively, a refined aptamer sequence can be elucidated by modifying a known aptamer structure (e.g., A22, SEQ ID NO: 12) using a software comprising "builder" type algorithms which utilizes a set of atomic coordinates defining a three-dimensional structure of the binding pocket and the three-dimensional structures of the basic aptamer (e.g., A22) to computationally assemble a refined aptamer. Ample guidance for performing rational drug design via software employing such "scanner" and "builder" type algorithms is available in the literature of the art (for example, refer to: Halperin I. et al., 2002. Proteins 47, 409-43; Gohlke H. and Klebe G., 2001. Curr Opin Struct Biol. 11, 231-5; Zeng J., 2000. Comb Chem High Throughput Screen. 3, 355-62; and RACHEL: Theory of drug design, http://wwwdotnewdrugdesigndotcom/Rachel_Theorydothtm#Software), and described in further detail hereinbelow.

Criteria employed by software programs used in rational drug design to qualify the binding of screened aptamer structures with binding pockets include gap space, hydrogen bonding, electrostatic interactions, van der Waals forces, to hydrophilicity/hydrophobicity, etc. Generally, the greater the contact area between the screened molecule and the polypeptide binding region, the lower the steric hindrance, the lower the "gap space", the greater the number of hydrogen bonds, and the greater the sum total of the van der Waals forces between the screened molecule and the polypeptide binding region of, the greater will be the capacity of the screened molecule to bind with the target polypeptide. The "gap space" refers to unoccupied space between the van der Waals surface of a screened molecule positioned within a binding pocket and the surface of the binding pocket defined by amino acid residues in the binding pocket. Gap space may be identified, for example, using an algorithm based on a series of cubic grids surrounding the docked molecule, with a user-defined grid spacing, and represents volume that could advantageously be occupied by a modifying the docked altamer positioned within the binding region of the polypeptide target.

Contact area between compounds may be directly calculated from the coordinates of the compounds in docked conformation using the MS program (Connolly M L., 1983. Science 221, 709-713).

Suitable software employing "scanner" type algorithms include, for example, docking software such as GRAM, DOCK, or AUTODOCK (reviewed in Dunbrack et al., 1997. Folding and Design 2, 27), AFFINITY software of the INSIGHTII package (Molecular Simulations Inc., 1996, San Diego, Calif.), GRID (Goodford P J., 1985. "A Computational Procedure for Determining Energetically Favorable Binding Sites on Biologically Important Macromolecules", J. Med. Chem. 28, 849-857; GRID is available from Oxford University, Oxford, UK), and MCSS (Miranker A. and Karplus M., 1991. "Functionality Maps of Binding Sites: A Multiple Copy Simultaneous Search Method", Proteins: Structure Function and Genetics 11, 29-34; MCSS is available from Molecular Simulations, Burlington, Mass.).

The AUTODOCK program (Goodsell D S. and Olson A J., 1990. Proteins: Struct Funct Genet. 8, 195-202; available from Scripps Research Institute, La Jolla, Calif.) helps in docking screened molecules to binding pockets in a flexible manner using a Monte Carlo simulated annealing approach. The procedure enables a search without bias introduced by the researcher. This bias can influence orientation and conformation of a screened molecule in the targeted binding pocket.

The DOCK program (Kuntz I D. et al., 1982. J Mol Biol. 161, 269-288; available from University of California, San Francisco), is based on a description of the negative image of a space-filling representation of the binding pocket, and includes a force field for energy evaluation, limited conformational flexibility and consideration of hydrophobicity in the energy evaluation.

Modeling or docking may be followed by energy minimization with standard molecular mechanics force fields or dynamics with programs such as CHARMM (Brooks B R. et al., 1983. J Comp Chem. 4, 187-217) or AMBER (Weiner S J. et al., 1984. J Am Chem Soc. 106, 765-784).

As used herein, "minimization of energy" means achieving an atomic geometry of a chemical structure via systematic alteration such that any further minor perturbation of the atomic geometry would cause the total energy of the system as measured by a molecular mechanics force-field to increase. Minimization and molecular mechanics force fields are well understood in computational chemistry (for example, refer to Burkert U. and Allinger N L., "Molecular Mechanics", ACS Monograph 177, pp. 59-78, American Chemical Society, Washington, D.C. (1982)).

Programs employing "builder" type algorithms include LEGEND (Nishibata Y. and Itai A., 1991. Tetrahedron 47, 8985; available from Molecular Simulations, Burlington, Mass.), LEAPFROG (Tripos Associates, St. Louis, Mo.), CAVEAT (Bartlett, Pa. et al., 1989. Special Pub Royal Chem Soc. 78, 182-196; available from University of California, Berkeley), HOOK (Molecular Simulations, Burlington, Mass.), and LUDI (Bohm H J., 1992. J. Comp Aid Molec Design 6, 61-78; available from Biosym Technologies, San Diego, Calif.).

The CAVEAT program suggests binding molecules based on desired bond vectors. The HOOK program proposes docking sites by using multiple copies of functional groups in simultaneous searches. LUDI is a program based on fragments rather than on descriptors which proposes somewhat larger fragments to match with a binding pocket and scores its hits based on geometric criteria taken from the Cambridge Structural Database (CSD), the Protein Data Bank (PDB) and on criteria based on binding data. LUDI may be advantageously employed to calculate the inhibition constant of a docked chemical structure Inhibition constants (Ki values) of compounds in the final docking positions can be evaluated using LUDI software.

During or following rational drug design, docking of an intermediate chemical structure or of a putative aptamer with the binding pocket may be visualized via structural models, such as three-dimensional models, thereof displayed on a computer screen, so as to advantageously allow user intervention during the rational drug design to optimize a chemical structure.

Software programs useful for displaying such three-dimensional structural models, include RIBBONS (Carson, M., 1997. Methods in Enzymology 277, 25), O (Jones, T A. et al., 1991. Acta Crystallogr. A47, 110), DINO (DINO: Visualizing Structural Biology (2001) http://wwwdotdino3ddotorg); and QUANTA, INSIGHT, SYBYL, MACROMODE, ICM, MOLMOL, RASMOL and GRASP (reviewed in Kraulis, J., 1991. Appl Crystallogr. 24, 946).

Other molecular modeling techniques may also be employed in accordance with this invention (for example, refer to: Cohen N C. et al, 1990. "Molecular Modeling Software and Methods for Medicinal Chemistry", J. Med. Chem. 33, :883-894; Navia M. A. and Murcko M. A., 1992. "The Use of Structural Information in Drug Design", Current Opinions in Structural Biology 2, 202-210). For example, where the structures of test compounds are known, a model of the test compound may be superimposed over the model of the structure of the invention. Numerous methods and techniques are known in the art for performing this step, any of which may be used (for example, refer to: Farmer P. S., "Drug Design", Ariens E J. (ed.), Vol. 10, pp 119-143 (Academic Press, New York, 1980); U.S. Pat. No. 5,331,573; U.S. Pat. No. 5,500,807; Verlinde C., 1994. Structure 2, 577-587; and Kuntz I D., 1992. Science 257, 1078-108).

In any case once putative aptamer sequences are identified they are examined for specific binding to the target polypeptide, which can be effected using a number of biochemical methods known in the art, such as a band shift assay (U.S. Pat. No. 5,756,291) and affinity chromatography [Schott, H., Affinity Chromatography, (Marcel Dekker, Inc., New York, 1984)].

Alternatively or additionally, the nucleic acid sequences of the present invention are tested for inhibiting influenza virus infection in vitro such as in MDCK cultured cell line, or in vivo as further described in Example 2 (in vitro) and Example 3 (in vivo) of the Examples section which follows.

As described hereinabove, an important constituent in aptamer design is selection of the polypeptide target. It is appreciated that peptides used for selecting the aptamer molecules of the present invention can be used as potent tools in influenza related therapeutic and diagnostic applications (13).

Thus, according to yet an additional aspect of the present invention there is provided a polypeptide useful for vaccination against an influenza virus (i.e., the orthomyoxiviruses).

The polypeptide of this aspect of the present invention includes an amino acid sequence which is preferably at least 60%, at least 70%, at least 80%, at least 85%, at least 90%, at least 92%, at least 94% or more, say 95%-100%, homologous to SEQ ID NO: 13 as determined using the BestFit software of the Wisconsin sequence analysis package, utilizing the Smith and Waterman algorithm, where gap creation penalty equals 8 and gap extension penalty equals 2 reflecting the conservation of the polypeptide among the various influenza strains and including functional homologues as well.

The polypeptide of this aspect of the present invention does not include the HA2 domain of influenza virus.

Preferably, the polypeptide of the present invention includes an amino acid sequence defined by amino acid coordinates 116-261 of SEQ ID NO: 14 which encompass the globular region of the influenza HA which mediates binding to host cell determinants such as the sialic acid receptors.

More preferably the polypeptide of the present invention includes an amino acid sequence defined by amino acid coordinates 116-245 of SEQ ID NO: 15 which encompass a further minimal globular region of the influenza HA.

Since the receptor binding pocket of influenza HA polypeptide is mostly unexposed to the immune system due to conformational restrictions, the polypeptide of this aspect of the present invention, preferably further includes additional antigenic epitopes such as defined by amino acid coordinates$_{91-261}$ of SEQ ID NO: 1 [McEwen (1992) Vaccine 10:405-411; Muller (1982) Proc. Natl. Acad. Sci. USA 79:569-573; Shapira (1985) J. Immunopharmacol. 7:719-723].

It will be appreciated that other antigenic epitopes, which are preferably conserved can be included in the polypeptide of the present invention, such as provided in Table 1, hereinabove.

Preferably, the polypeptide of this aspect of the present invention is as set forth in SEQ ID NOs: 13-15.

Alternatively, the polypeptide of this aspect of the present invention includes the amino sequence set forth in SEQ ID NOs: 13-15.

The term "polypeptide" as used herein encompasses native peptides (either degradation products, synthetically synthesized peptides or recombinant peptides) and peptidomimetics (typically, synthetically synthesized peptides), as well as as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |

TABLE 3-continued

| Non-conventional amino acid | Code | Non-conventional amino acid | Code |
|---|---|---|---|
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclicization does not severely interfere with peptide characteristics, cyclic forms of the peptide can also be utilized.

The present inventors have conclusively shown that polypeptides generated according to the teachings of the present invention are capable of eliciting humoral and cellular immune responses (see Examples 7-8 of the Examples section).

It is well appreciated that DNA immunization generates a better cellular immune response to many viral agents as compared to peptide immunization.

Thus according to still an additional aspect of the present invention there is provided an isolated polynucleotide encoding the polypeptide of the present invention, described hereinabove.

The polynucleotide may constitute a genomic, complementary or composite polynucleotide sequence encoding the polypeptide of the present invention.

As used herein the phrase "complementary polynucleotide sequence" includes sequences, which originally result from reverse transcription of messenger RNA using a reverse transcriptase or any other RNA dependent DNA polymerase. Such sequences can be subsequently amplified in vivo or in vitro using a DNA dependent DNA polymerase.

As used herein the phrase "genomic polynucleotide sequence" includes sequences, which originally derive from a chromosome and reflect a contiguous portion of a chromosome.

As used herein the phrase "composite polynucleotide sequence" includes sequences, which are at least partially complementary and at least partially genomic. A composite sequence can include some exonal sequences required to encode the HA globular region, glycosylation consensus sites, as well as some intronic sequences interposed therebetween. The intronic sequences can be of any source, including of other genes, and typically will include conserved splicing signal sequences. Such intronic sequences may further include cis acting expression regulatory elements. Intronic sequences may also contribute to the translated protein.

As shown in Example 7 of the Examples section which follows, antibodies generated against the polypeptides and polynucleotides of the present invention cross-react with multiple influenza strain species and as such can be used in various clinical applications.

Thus, according to a further aspect of the present invention there is provided an antibody or antibody fragment, which includes an antigen binding site specifically recognizing the polypeptide of the present invention, described hereinabove.

As used herein the term "antibody", refers to an intact antibody molecule and the phrase "antibody fragment" refers to a functional fragment thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

As mentioned hereinabove, the polypeptides and nucleic acid sequences of the present invention can be used for treating influenza infection.

Thus according to yet a further aspect of the present invention there is provided a method of treating influenza virus infection.

The method is effected by providing to a subject in need thereof, a therapeutically effective amount of the polypeptide, polynucleode and/or antibody of the present invention, described hereinabove.

Preferred administration routes and pharmaceutical compositions are described hereinabove.

It will be appreciated that antibodies generated according to the teachings of the present invention can be used also for identifying influenza virus in a biological sample.

The method can be effected by contacting a biological sample such as described hereinabove, with the antibody or antibody fragment of the present invention.

Thereafter, immunocomplexes including the antibody or antibody fragment in the biological sample are detected, to thereby identify the influenza virus in the biological sample.

Preferably, immunocomplexes are washed prior to detection to remove any non-specifically bound antibodies, allowing only those antibodies specifically bound within the primary immune complexes to be detected.

In general detection of immunocomplex formation is well known in the art and may be achieved by any one of several approaches. These approaches are generally based on the detection of a label or marker, such as described hereinabove.

The nucleic acid molecules, conjugates thereof, polynucleotides, polypeptides and antibodies generated according to the teachings of the present invention can be included in a diagnostic or therapeutic kit. These reagents can be packaged in a one or more containers with appropriate buffers and preservatives and used for diagnosis or for directing therapeutic treatment.

Thus, nucleic acid molecules and conjugates thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The nucleic acid molecules and conjugates thereof of such kits can also be attached to a solid support, as described and used for diagnostic purposes. The kit can also include instructions for determining if the tested subject is suffering from, or is at risk of developing influenza infection.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Hemagglutinin-Specific Aptamers—Rationale and Design

Systematic Evolution of Ligands by Exponential Enrichment (SELEX) was effected, in order to identify aptamer oligonucleotides which bind the influenza Hemagglutinin (HA).

Materials and Experimental Procedures

Library generation—The aptamer library containing a central randomized sequence of 30 nucleotides flanked by a common 5' sequence—AAT TAA CCC TCA CTA AAG GG (SEQ ID NO: 16, denoted as T3, Stratagene, La.) and a common 3' sequence—5'-TAT GGT CGA ATA AGT TAA-3' (SEQ ID NO: 17) was synthesized in a 380B DNA synthesizer (Applied Biosystems). The library included a 30 nucleotide random segment, over all $10^{16}$ molecules and generated according to manufacturer's instruction (Applied Biosystems).

SELEX—ssDNA aptamers were denatured at 80° C. for 10 min and then cooled on ice for 10 min Aptamers 30 nmole were mixed with 25 µg of $HA_{91-261}$ peptide (Further described hereinbelow) in 500 µl selection buffer (50 mM Tris-HCl; pH 7.4, 5 mM KCl, 100 mM NaCl, 1 mM $MgCl_2$ tRNA, 0.2% BSA) at 37° C. for 30 min. Aptamer-peptide complex was purified by adding the 25 µl Ni-NTA superflow (Qiagen, Hilden, Germany) and amplified by PCR using primers directed to the common sequences in the aptamer library [i.e., 5'-AAT TAA CCC TCA CTA AAG GG-3', SEQ ID NOs. 18 (T3) and 3' primer 5' TTA ACT TAT TCG ACC ATA-3', SEQ ID NOs. 19]. SELEX was repeated 3 times, following which amplified nucleotides were transformed into *E. coli*. PCR conditions for SELEX included 5 min 95° C./1 min 95° C./1 min 55° C./1 min 72° C./10 min 72° C. and 100 pmole of each primer.

Reverse screening of aptamer—Selected ssDNA molecules from each individual clone were biotinylated using the B-T3 (Stratagene, La Jolla, Calif.), which is same sequence with 5' primer (T3 primer), and klenow fragment (2 unit/ml). To prepare single stranded biotin conjugated A22 aptamer for the reverse screening. T3 Primer (SEQ ID NO: 18) was Biotin labelled (Stratagene, La Jolla, Calif.).

A 96-well flat bottom ELISA plate (Nunc, Denmark) was prepared by coating each well with 100 µl of streptavidin (100 µg/ml) diluted in 0.1 M $NaHCO_3$ following by a 37° C. overnight incubation. Following several washings with PBS, wells were blocked with 200 µl of PBS containing 1% BSA for 2 hours at room temperature and subsequent washing three times with PBS-T (10 mM PBS containing 0.05% (v/v) Tween-20). Thereafter, 100 µl of 2.5 pmole/100 µl biotinylated—ssDNA were added to the wells and incubated at 37° C. for 2 hours followed by washing four times with PBS-T. T3 primer primer was used as negative control (SEQ ID NO: 18). Following washing, 100 µl of 10 Hemagglutinin Unit (HAU) of influenza virus or 2 µg histidine labelled $HA_{91-261}$ peptide were added to the indicated wells and incubated at 37° C. for 2 hours. The wells were then washed for 4 times with PBS-T, and anti-histidine antibodies (Qiagen, Hilden, Germany) and anti-virus antibodies (serum samples from to mice immunized with recombinant $HA_{91-261}$) were added to the corresponding wells. The reverse screening assay was completed by ELISA.

Enzyme-linked Immunosorbent Assay (ELISA)—High binding capacity ELISA plates (Immunoplate, Nunc, Denmark) were coated with 100 µl allantoic fluid containing 100 HAU/ml of various influenza virus strains diluted in phosphate buffered saline (PBS) by incubating at 4° C. overnight. Following several washing steps with PBS, wells were blocked with 200 µl of PBS containing 1% bovine serum albumine (BSA) and incubated for 90 min at room temperature. Plates were then washed three times with PBS containing 0.05% (v/v) Tween-20 (PBS-T). Each well was then supplemented with 100 µl serial diluted serum samples and incubated at 37° C. for 2 hours. Following this incubation period, plates were washed five times in PBS-T and bound antibodies were detected using horseradish peroxidase labelled goat anti-mouse IgG conjugates (HRP; Jackson Laboratories) Immunocomplexes were visualized by incubating with 3,3',5,5'-Tetramethyl benzidine solution (TMB, Zymed) for 30 min at room temperature. Reaction was terminated with 50 µl of 2M $H_2SO_4$, plates were read with a multichannel spectrophotometer (Titertek, Multiskan MCC/340 MK II, Lab system, Finland) at 450 nm.

Results

In order to identify oligonucleotides which bind to the amino $acids_{91-261}$ of the HA molecule, a nucleotide library containing random 30 nucleotides between conserved linkers, was synthesized. The library included $10^{18}$ types of different ssDNA, which were hybridized to the $HA_{91-261}$ peptide and purified by Ni-NTA resin. Following purification, ssDNAs were amplified by PCR using the linker sequences. The process was 4 times repeated, and re-screening of the $HA_{91-261}$-bound was effected by ELISA.

This reverse-screening process resulted in two oligonucleotide aptamers denoted as 'A21' and 'A22' (SEQ ID NOs. 11 and 12, respectively). A21 and A22 showed the same binding capacity to $HA_{91-261}$, however a significant difference in binding the intact virus was evident (FIGS. 2*a-b*). Therefore, structural and functional analysis of the A22 oligonucleotide only was further effected. Proposed secondary structures using DNAdraw program (18) for A22, A21 and a control oligonucleotide are shown in FIGS. 2*c-e*.

Example 2

In-Vitro Aptamer Protection from Influenza Infection

The protective effect of the A22 aptamer against influenza infection (the H3N2 Port Chalmers strain) was investigated in vitro using MDCK cells (19).

Materials and Experimental Procedures

Viruses—Influenza strains A/Port Chalmers/1/73 (H3N2), A/Texas/1/77 (H3N2), PR/8/34 (H1N1) and Japanese/57 (H2N2) were grown in the allantoic cavity of 11-day-old embryonated hen eggs (Bar On Hatchery, Hod Hasharon, Israel). Virus growth and purification were performed according to standard methods described by Barret and Inglis (23). Titration of virus in the allontoic fluid was performed by an haemagglutination assay.

Cells—Madin-Darby Canine Kidney cells (MDCK, ATCC #CCL 34) were maintained in Dulbecco's modified Eagle's medium (DMEM) supplemented with heat inactivated 10% fetal calf serum (FCS).

MTT assay—MDCK cells were plated in 96 well plates ($7 \times 10^4$/well) one day prior to the assay. Cells were washed twice with Dulbecco's phosphate buffered saline (DPBS) prior to a 1 hour incubation with Hank's balanced salt solution (HBSS) supplemented with 25 mM HEPES and 4 mM sodium bicarbonate (pH 7.3) including 10 HAU of Port Chalmers/1/73 (H3N2) or 10 HAU of Japan (H2N2) in the presence or absence of the indicated aptamer concentration. Following infection, cells were incubated in growth medium at 37° C. for 72 hours. MTT assay was performed by adding 4 mg/ml MTT (3-[4,5-Dimethylthiazol-2-yl]-2,5-diphenyltetrazolium bromide, Sigma, St. Louis, USA) dissolved in PBS to the cell cultures and incubation at 37° C. for 3 hours. Plates were then centrifuged at 800×g for 10 min. Supernatants were aspirated and the formazan dye was dissolved in 150 ul/well of isopropyl alcohol (Merck, Darmstadt, Germany), and O.D values were determined with an ELISA reader at 540 nm.

In vitro viral protection prior to viral infection—MDCK cells were plated on 96 well plates ($7\times10^4$/well) 24 hours prior to the experiment. Each well was washed twice with DPBS prior to treating the cells with 50 pmole A22 at 37° C. for the indicated time points. Cells were then washed twice with DPBS and infected with 10 HAU H3N2 for 1 hour in enriched HBSS. Following incubation, cells were to transferred to growth medium and incubated at 37° C. for 72 hours. Thereafter an MTT assay was effected as described.

In vitro viral protection following viral infection—MDCK cells were plated on 96 well plates ($7\times10^4$/well) 24 hours prior to viral infection. Viral infection was effected as described above. Infected cells were gently washed with DPBS for 3 times. Cells were then treated with 50 pmole A22 for 1 hour at 37° C. Following incubation, cells were transferred to growth medium and incubated at 37° C. for 72 hours. Thereafter an MTT assay was effected as described.

Immunostaining—$5\times10^5$ MDCK cells were laid on glass cover slips. Following 24 hr, influenza virus (Port Chalmers/1/73, H3N2) was added with or without 1 hr preincubation with A22. Following another 48 hrs, cells were permeabilized with 3% paraformaldehyde containing 0.5% Triton X-100 and subsequently fixed with freshly prepared 3% paraformaldehyde. Influenza surface antigen haemagglutinin was detected by incubating the cultures with a mouse monoclonal antibody specific for influenza haemagglutinin (diluted 1:100, Santa Cruz Biotechnology Inc.) All antibody incubations were effected for 1 hr at room temperature in a humidified chamber, followed by three washes in PBS. Primary antibodies were detected with Cy3 conjugated goat anti-mouse immunoglobulin (Jackson Immunoresearch Laboratories, USA) secondary antibodies. Nuclei were visualized by staining with 2 μg/ml 4',6-diamidino-2-phenylindole (DAPI; Sigma, Israel) Immunofluorescence microscopy was performed using a Nikon Eclipse E600 microscope. Photographs were taken by using Spot software programme. Images were processed with Adobe Photoshop (Adobe Systems, Mountain View, Calif.).

Results

Aptamer ability to in-vitro protect cells from influenza virus infection was tested. As shown in FIG. 3*a*, cells treated with aptamer A22 prior to viral infection (H2N2) demonstrated a significant reduction in virus associated cell-death. Interestingly, the protective effect peaked at a concentration between 50 and 100 pmole of A22, probably due to the high concentrations on non-infected cells (FIG. 3*b*). Accordingly, the effect of 50 pmole A22 on the infection of an additional viral strain H3N2 was studied. As shown in FIG. 3*b*, A22 elicited an approximate protection of 60% and 70% against infection of the cells with H2N2 and H3N2, to respectively, when compared to non-infected MDCK cells. Interestingly, as also shown in FIG. 3*b*, A21 aptamer was also capable of reducing the in vitro infectivity of the viruses, as compared to a non-relevant oligonucleotide control, which did not reduce cell mortality at all.

The ability of the A22 aptamer to bind host proteins was then determined. Prior to viral infection, MDCK cells were incubated with A22 (50 pmole) for 30 min or 60 min, followed by repeated washing. As shown in FIG. 3*c*, no significant difference between the survival rate of non-treated and treated cells was evident, nor any difference between two exposures of the cells to A22 (i.e., prior to and following viral infection) could be detected. These results suggest that the inhibitory activity of A22 is not due to direct blocking the sialic-acid containing receptors on host cells.

In order to examine whether A22 is still protective if added following binding of the virus to the host cell receptors, MDCK cells were incubated with 10 HAU H3N2 virus for 30 min or 60 min prior to the treatment with 50 pmole A22. As shown in FIG. 3*d*, following 60 minute incubation with the virus the effect of A22 was not significant. In contrast, the difference between non-infected cells and cells incubated with virus for 60 minutes was significant ($p=0.0028$). Notably, a highly significant difference was observed between the infected cells and those incubated with the virus for only 30 min prior to treatment with A22. Thus, these results suggest A22 cannot prevent cell-death once virus-host cell receptor interaction has reached its optimum.

The effect of A22 in preventing viral binding and entry to cells was also demonstrated by microscopy analysis. As seen in FIGS. 4*a-c*, using light microscopy, the whole morphology of the MDCK cells was damaged by the viral infection (FIG. 4*a*). In comparison, in the presence of A22, destruction was inhibited and the cell morphology was largely conserved (FIG. 4*b*). Furthermore, the mere treatment with A22 did not affect the morphology of the cells (FIG. 4*c*), indicating that the damage was caused only by the virus. These findings were further substantiated by immunofluorescence monitoring the viral presence using Cy3 labeled specific anti-HA monoclonal antibodies. As shown, whereas viral presence is clearly manifested in the infected cells (FIG. 4*d*), it is almost entirely prevented by addition of A22 (FIG. 4*e*). Untreated cells appeared identical to the cells treated with A22 (FIG. 4*f*).

Example 3

In-Vivo Aptamer Protection from Influenza Infection

The protective effect of the A22 aptamer against influenza infection (the H3N2 Port Chalmers strain) was investigated in infected mice.

Materials and Experimental Procedures

Mice—BALB/c mice at the age of 10-12 weeks were purchased from Harlan Laboratories (Rehovot, Israel).

Animal infection—Mice were inoculated intranasally with sublethal infectious allantoic fluid containing 100 HAU Port Chalmers/1/73 (H3N2) virus with or without 2.5 nmole A22 aptamer for different time intervals. Mouse body weight was monitored for 2 weeks. Viral titer in the lungs was determined by the egg titration method (19). Briefly, mice were sacrificed 6 days following viral inoculation and lungs were removed and homogenized in PBS 0.1% BSA (10% w/v). Following homogenization, samples were centrifuged to remove debris and stored at −70° C. At the day of the experiment, thawed lung homogenates were injected (100 μl of 10 fold serial dilution) into the allantoic cavity of 9-11 days old embryonated eggs. Following incubation for 48 h at 37° C. and overnight at 4° C., allantoic fluid was removed and virus presence was determined by hemagglutination assay. The results of these assays were presented as log EID$_{50}$ (26).

Haemagglutination Assay—Chicken red blood cells (CRBCs) were diluted in Alsevier solution to reach a final concentration of 0.5%. Assay was performed in micro-titer plates containing 50 μl sample and 50 μl of 0.5% CRBCs. The results of assay were presented as Log EID$_{50}$ at the end of 90 min incubation.

Histology—For lung histology, mice were sacrifised at day 7 and lungs were removed into 10% neutral bufferd formalin (pH 7.0). Lungs were then sectioned and stained with haemotoxylin and eosin. Slide were viewed by a non-informed observer.

Statistical Analyses—Statistical analysis was performed by using Student's t-test with p<0.05 considered as statistically significant.

Results—The antiviral properties of A22 were determined in vivo prior to and following viral infection. Briefly, mice were divided into four groups designated 'untreated', '0 day', '−1 day' and '+2 day'. Each mouse was challenged with 100 HAU of influenza A/Texas/1/77 virus. Mice in '0 day' group were inoculated with a to mixture of the virus and 2.5 nmole/ml A22, intranasally (i.n). Mice in '−1 day' and '+2 day' groups were inoculated with 2.5 nmole/ml A22, i.n 1 day prior to, or 2 days following virus infection, respectively. Influenza infection was monitored by three parameters, including (i) Body weight loss during 16 days following virus treatment; (ii) Lung virus titre; (iii) Histological examination of lungs—sections were taken 7 days following virus inoculation.

In contrast to non-infected mice (FIG. 5a), infected mice showed typical pathology including bulk expansion of mononuclear cells and collapsed areas (FIG. 5b). In comparison, in lungs of A22 treated mice especially in the '0 day' and '−1 day' groups, (FIG. 5c and FIG. 5d, respectively) a much less mononuclear cell infiltration was evident and most of the alveoli remained open. Interestingly, in the '+2 day' group both damaged and non-damaged sites could be observed (FIGS. 5e-f). These findings suggest that administration of A22 reduces the inflamed areas in lungs. Furthermore, compared to control group, treatment groups (+2 day, 0 day and −1 day) showed significantly lower weight loss and enhanced recovery (FIG. 6a).

The protective capacity of A22 was also investigated using the whole egg titration method (20) measuring the viral load in lungs of mice. As shown in FIG. 6b, mice treated with 2.5 nmole/ml A22 (125 pmole/mice) for different time intervals demonstrated protective effect against viral challenge as compared to non-treated mice. The protective effect in the '0 day group' was the most prominent, manifested in more than 2 log difference in lung virus titer compared to the non-treated group, which is equivalent to over 99% protection. No significant difference in the A22 protective effect between '+2 day' and '−1 day' groups was observed.

These results suggest that A22 is effective before and even several days after the infection. It will be appreciated that since only low concentrations of A22 were used in this protection experiment (nmole/ml concentration), it is concievable that the protective effect of A22 could be further increased.

Example 4

Aptamer Treatment Confers Protection Against Infection by Various Influenza Strains Since the receptor binding region of the HA is a highly conserved region, it was of interest to test whether the protective effect of A22 is manifested also towards infection with other influenza strains. It was also of interest to compare the effect of the aptamer to that of a currently available anti-influenza therapy, the neuraminidase inhibitor, Oseltamivir.

Materials and Experimental Procedures

Materials—Oseltamivir was purchased from Roche, Basel, Switzerland.

Animals and infection procedures—were effected as described hereinabove,

Results

The results are shown in FIG. 7a, which demonstrates the reduction in the lung virus titer in mice infected with three strains of influenza, as a result of treatment with A22 on the day of infection. It is noteworthy that A22 is efficient in preventing the infection by all tested strains A/PR/8/34 (H1N1), A/Japanese/37 (H2N2) as well as A/Texas/1/77 (H3N2). These findings corroborate the results of the in vitro assay presented in FIG. 3b. In contrast to A22, a control irrelevant nucleotide, coding for influenza Nucleoprotein region NP 147-158 (SEQ ID NO: 22), led to an insignificant change in the viral titer. It is of interest that the aptamer A21, although less effective than A22 was still capable of reducing the lung virus titer of A/Texas/1/77 (H3N2, see FIG. 7b).

The ability of the A22 aptamer to inhibit influenza infection was also compared to that of one of the currently available anti-influenza drugs, the Neuraminidase inhibitor Oseltamivir. To this end, both A22 and Oseltamivir were administered once, together with the virus, using the intranasal. route. As is shown in Table 4 below, a dose of 20 μg/mouse of Oseltamivir (1 mg/kg body weight) reduced virus titer by 0.62 log EID50, representing a 4.17 fold reduction in virus burden. This is in comparison to a reduction by 1.1 log EID50 affected by A22 in this particular experiment (over 10 fold reduction in virus burden.

TABLE 4

| Treatment | Δlog EID50 | Fold reduction | Protection (%) |
|---|---|---|---|
| A22 | 1.11 | 12.88 | 92.3 |
| Oseltamivir | 0.62 | 4.17 | 76.03 |

Altogether these results suggest a mechanism of action for the aptamer sequences of the present invention, essentially, direct binding to the receptor binding region of the HA on the virus cell surface, to thereby prevent attachment of the virus to the host cell and consequently viral entry to the host cell.

Example 5

Aptamer Cross-Reactivity with Multiple Influenza Strains

Cross-reactivity of the A22 aptamer of the present invention towards multiple influenza strains was determined using an ELISA assay.

Materials and experimental procedures—Effected as described in Example 1.

Results

Since the DNA aptamer of the present invention was designed based on the conserved sequence of $HA_{91-261}$, the cross reaction between the $HA_{91-261}$ and various influenza strains was determined by ELIZA. As shown in FIGS. 8a-e, antibodies generated against the conserved peptide cross reacted with all influenza strains under investigation thereby substantiating the conservation of the peptide and supporting the the global potential of the aptamer drugs of the present invention.

Example 6

Generation and Characterization of Recombinant $HA_{91-261}$ Peptide

Experimental Procedures

Generation of $HA_{91-261}$ peptide by RT-PCR—Total RNA of influenza strains A/Port Chalmers/1/73 virus was isolated and used for reverse transcriptase (RT)-PCR employing two primers corresponding to residues 91-97 and 255-261 of HA protein; 5'-GGA TCC AGC AAA GCT TTC AGC AAC TGT-3' (SEQ ID NO: 20) and 5'-GTC GAC GCG CAT TTT GAA GTA ACC CC-3' (SEQ ID NO: 21), respectively and Taq Polymerase (Invitrogen, Carlsbad, Calif.). The resultant PCR product, which codes for part of the globular region of HA protein ($_{91-261}$ amino acid), was verified by DNA sequence analysis. The PCR product was then cloned into the pQE30 plasmid (Qiagen, Hilden, Germany) for overexpression of the gene product in *E. coli*. An overexpressed peptide obtained by IPTG induction for 5 hr was purified using Ni-NTA column (Qiagen). The PCR product was further cloned into pCDNA3.1 HisC plasmid (Invitrogen, Carlsbad, Calif.) for injection in mice muscles. For immunization studies, plasmid DNA was amplified using the Endofree plasmid Giga kit (Qiagen).

Results

DNA constructs coding the $HA_{91-261}$ region of influenza viral RNA were generated for mammalian and bacterial expression. To this end, a cDNA fragment encoding $HA_{91-261}$ sequence was amplified by PCR from the influenza A virus (i.e., H3N2) using primers corresponding to amino acid residues 91-97 and 255-261 of influenza HA (SEQ ID NOs. 20 and 21, respectively). The resultant PCR product was cloned into the pQE30 plasmid and the N-terminal portion thereof was tagged with 6 His residues in frame for the purification. Overexpressed and purified $HA_{91-261}$ protein fragment migrated as a 25 kDa band in 12% SDS-PAGE, as shown in FIG. 9a.

The antigenicity of $HA_{91-261}$ was confirmed by an ELISA assay with specific rabbit antibodies raised against $HA_{91-108}$ peptide or with rabbit antiserum against influenza virus (FIG. 9b).

For DNA vaccination PCR product encoding the $HA_{91-261}$ peptide, was cloned into a $pHA_{91-261}$ mammalian expression vector and expressed in mice cells under the CMV promoter. The BamHI/SalI fragment of PCR product were confirmed by DNA sequencing analysis before insertion into the BamHI/XhoI site of pCDNA3.1 HisC vector, under the ATG start codon and N-terminal 6 His residues in frame.

Example 7

Humoral Immune Response Generated by Peptide and DNA Vaccination

Materials and Experimental Procedures

Immunization and infection procedures—Groups of 8-10 mice were immunized intramuscularly (i.m.) with 100 μg of plasmid DNA encoding the $HA_{91-261}$. Mice were boosted twice, at 3-week intervals, using the same amount of antigen as used for the initial immunization.

For the immunization against the $HA_{91-261}$ peptide, 50 μg peptide per animal in 50 μl PBS was administrated to the nostrils of mice lightly anesthetized with ether (i.n.) or injected in the foot-pads with same peptide in complete Freund's adjuvant (CFA). For the combined use of peptide and DNA vaccine (combined DNA priming-protein boosting), the mice were injected twice i.m. using plasmid $pHA_{91-261}$ and then boosted with $HA_{91-261}$ peptide intranasally.

Infection of mice was performed 1 month following the last booster, by intranasal inoculation of infectious allantoic fluid containing 1 HAU influenza virus per mouse under light ether anesthesia.

Serum and Lung homogenates preparation—In order to measure production of specific anti-influenza antibodies in immunized mice, sera for IgG assays were generated from blood collected 3-weeks following the second and third immunizations. The supernatant fluid from lung homogenates (suspended in 0.1% BSA in PBS) were collected for IgA assay and determination of lung virus titre.

Statistical analysis—Statistical analysis was effected using the Stat-View II software (Abacus Concepts, Berkeley, Calif.). Fisher PLSD test was utilized to calculate probability (p) values. Results are presented as mean and standard error of at least two repeated independent experiments.

Results

Humoral immune responses induced by different vaccinations—$HA_{91-261}$ peptide and DNA preparations, described hereinabove, were administered to mice in order to determine the ability thereof to induce antibodies.

Two weeks following the last immunization, lung homogenates from mice immunized with either the $HA_{91-261}$ peptide or plasmid $pHA_{91-261}$ (2 mice per group) were collected for determination of IgA level. In order to determine IgG levels in immunized mice, an IgG assay was performed. Briefly, sera were prepared from blood collected 3-weeks following the third immunizations. The samples of each group were pooled together and assayed by ELISA for the presence of antibodies reactive with $HA_{91-261}$ peptide, as well as those recognizing the intact virus. As shown in FIG. 10a, only immunization via foot-pad with the $HA_{91-261}$ peptide elicited IgG antibodies, while no detectable IgG antibodies which recognized $HA_{91-261}$ peptide were observed after intranasal immunization. However, significant levels of IgG antibodies which recognized the intact virus (FIG. 10b) were still observed following intranasal immunization with $HA_{91-261}$ peptide without any adjuvant.

As shown in FIG. 10c, antibodies induced by $HA_{91-261}$ peptide showed to cross-reactivity with different influenza viral strains including H1N1 (PR/8/34) and H2N2 (Japanese/57).

Interestingly, immunization with the DNA plasmid $pHA_{91-261}$ did not elicit antibody response (FIG. 10a).

As shown in FIG. 11a, neither the $HA_{91-261}$ peptide, nor the $pHA_{91-261}$ plasmid could elicit the production of IgA antibodies which recognize the peptide fragment. However, mice immunized with $HA_{91-261}$ peptide produced significant levels of IgA antibodies recognizing the intact virus (FIG. 11b). In contrast, no IgA response in was detected in mice immunized with pHA$_{91-261}$ plasmid.

Thereafter, the ability of both HA$_{91-261}$ peptide and DNA to produce a synergized or additive antibody response was addressed. To this end, DNA priming followed by protein boosting immunization regimen was effected. As shown in FIGS. 10a-c and 11a-b, combined injection of DNA and peptide vaccine elicited significant levels of IgG and IgA antibodies against intact virus, however, with no apparent additive effect as compared to injection with the HA$_{91-261}$ protein fragment alone.

Thus, these results indicate that both peptide and DNA vaccines generated according to the teachings of the present invention induce humoral immune response, although a significantly higher antibody production was evident upon immunization with the peptide as compared to the DNA encoding thereof.

Furthermore, the cross reactivity of IgG antibodies with different influenza strains suggests that the HA$_{91-261}$ globular region of the HA molecules may lead to universal vaccination.

The ability of the vaccines of the present invention to induce IgA and IgG antibodies is of special significance, since while IgG are considered to be produced in the serum, IgA antibodies are mainly produced in the lung, where they can exert an important local anti-influenza effect. These results are further substantiated in light of the findings that in respiratory tract diseases vaccine protection is correlated with increased respiratory tract secretory IgA [Lue (1988) J. Immunol. 140:3793-3800; Nedrud (1987) J. Immunol. 139: 3484-3492].

Example 8

Cellular Immune Response Generated by Peptide and DNA Vaccination

Materials and Experimental Procedures

Splenocyte proliferation assay—BALB/c mice were immunized with 50 μg/50 μl HA$_{91-261}$ peptide without adjuvant (i.n.) or with 100 μg pHA$_{91-261}$ plasmid in PBS (i.m.) for 3 times at 3-week intervals as described above. The spleens were dissected 14 days following third immunization and proliferative response to the HA$_{91-261}$ peptide was tested. The cells were cultured in 96-well flat-bottomed plates (Nunc, Denmark) using triplicates of 0.2 ml cultures containing 5×10$^5$ cells/well in RPMI-HEPES (Sigma, St.Louis, USA). Splenocytes were stimulated with the indicated concentrations of the HA$_{91-261}$ peptides or inactivated purified virus and cultured for 48 hours. The cells were pulsed with 1 mCi (37 Bq) of [$^3$H] thymidine (Amershampharmacia, UK) overnight. Thymidine incorporation was determined in a Packard β-counter.

Cytokine assay—Antibodies and purified cytokines were obtained from Phamingen (San Diego, Calif.). The purified anti-cytokine capture mAbs diluted to 2 μg/ml (rat anti-mouse IL-4) or 4 μg/ml (rat anti-mouse IL-2, IL-10, and IFN-γ) in carbonate buffer (0.1 M NaHCO$_3$, pH 8.2) were coated to ELISA plate, and incubated for overnight at 4° C. Following a wash with PBS-Tween (10 mM PBS containing 0.05% Tween-20), the plates were blocked with PBS including 10% fetal calf serum (Biological Industries, Israel) at 200 μl per well for 2 hours at room temperature. Standard and diluted samples were added to wells and incubated for overnight at 4° C. Plates were washed and biotinylated anti-cytokine detecting mAb in PBS/10% serum was added to each well for 1 hour. Peroxidase-conjugated avidin was then added and the assay proceeded using the same steps as those described for ELISA. The cytokines were quantitated by comparison with a standard curve of purified cytokines captured and detected as above.

Cytotoxic T lymphocyte (CTL) assays—CTL killing assays were performed essentially as described by Zweerink et al., (1977, Eur. J. Immunol. 7:630-635). Briefly, spleen cells from mice immunized with HA$_{91-261}$ peptide and/or pHA$_{91-261}$ DNA were stimulated for five days with syngenic naive spleen cells infected in vitro with influenza A/Texas/77 virus. P815 target cells (ATCC TIB 64) were incubated with radioactive sodium chromate ($^{51}$Cr, 5 μCi to 10$^6$ cells), and influenza virus for 90 min at 37° C., 5% CO$_2$ in RPMI+ HEPES (n-(2-hydroxyethyl)piperazine n'-(2-ethane sulfonic acid). The effector spleen cells were harvested, washed, and incubated with the thoroughly washed target cells at various killer to target ratio for 5 hr at 37° C. Target cell lysis was monitored by $^{51}$Cr-release to the medium, and presented as percentage of the total release (measured by lysis of the target cells by 1% Sodium Dodecyl Sulphate, SDS) after correction for the spontaneous release.

Results

Induction of proliferative splenocyte response by the HA$_{91-261}$—To evaluate the efficacy in priming T helper activity, the cellular immune response in the spleens of immunized mice was tested by thymidine incorporation. As shown in FIG. 12a, splenocytes from peptide immunized mice highly proliferated upon co-incubation with the HA$_{91-261}$ peptide. Interestingly, this cellular response towards the HA$_{91-261}$ peptide was dose dependent as shown by interaction with the indicated concentrations of HA$_{91-261}$ peptide (i.e., 5 to 20 μg/ml and stimulation of 3.1/5 μg, 4.7/10 μg, and 6.2/20 μg). The mice immunized with HA$_{91-261}$ peptide showed also positive proliferative responses to the intact virus (FIG. 12b). In contrast, the proliferative responses that were observed in the splenocytes from mice immunized with the DNA fragment were hardly detectable. Upon combined DNA priming-protein boosting, a positive response was notable only to the intact virus and even in this case, the response was not higher than that obtained with the HA$_{91-261}$ peptide alone (FIG. 12b).

To characterize the T cell subtype produced following immunization with HA$_{91-261}$ peptide, the cytokine release profile was determined. As shown in FIGS. 13a-b, only spleen cells from mice immunized with the HA$_{91-}$ secreted significant levels of IL-2 (FIG. 13a) and IFN-γ (FIG. 13b), in response to both the purified peptide and the intact influenza virus, indicating that these lymphocytes belong to the Th1 subtype. This cell subtype is related to the antibody-dependent cell mediated cytotoxicity and clearance of infected cells. In contrast, IL-4 and IL-10 which represent Th2 responses, were undetectable (data not shown). No cytokine secretion at all was observed by cells from mice immunized with DNA or a peptide combination thereof.

Induction of CTL responses by pHA$_{91-261}$ DNA immunization—To activate CTL memory cells, spleen cells from mice immunized with the pHA$_{91-261}$ DNA construct or the HA$_{91-261}$ peptide were stimulated with antigen presenting cells infected with influenza virus. The resulting effector cells were co-incubated in vitro with $^{51}$Cr labeled P815 target cells which were either untreated or infected with virus at various effector to target cell ratio.

As shown in FIGS. 14a-b, CTLs were evident only following virus-stimulation in mice immunized with the DNA construct, leading to specific lysis of virus-infected target cells.

No such response was observed in mice immunized with $HA_{91-261}$ peptides or the combined DNA priming-protein boosting.

CTL activity induced by DNA vaccination is in accord with previous findings substantiating a preferred CTL response to viral antigens following DNA vaccination [Raz (1996) Natl. Acad. Sci. USA 93:5141-5145; Ulmer (1993) Science 259: 1745-1749]. For example, induction of class I-restricted CTL and protection of mice against heterologous virus challenge has been demonstrated with plasmid DNA encoding NP or HA [Johnson (2000) J. Gen. Virol. 81:1737-1745].

Altogether these results suggest differences in the pathway of immune responses elicited by the DNA and peptide fragments corresponding to the same region of the HA molecule.

Example 9

HA Peptide Immunization Protects from Influenza Virus Infection

Materials and Experimental Procedures

Protection assay against viral challenge—One month following immunization, immunized mice were administered with an i.n. inoculation of infectious allantoic fluid containing 1 HAU/mouse. Following 5 days, mice were sacrificed and Lungs and blood samples were retrieved and stored at –70° C., as described above) Immediately prior to the assay, lungs were thawed, homogenized in PBS 0.1% BSA (10% w/v) and centrifuged in order to remove debris. Virus titres were determined by the whole egg titration method [Fayolle (1991) J. Immunol. 147:4069-4073]. Lung homogenates (100 µl of 10-fold serial dilutions) were injected into the allantoic cavity of 9-11 days old embryonated eggs. Following incubation for 48 hours at 37° C. and overnight at 4° C., allantoic fluid was removed and virus presence was determined by haemagglutination, in micro-titre plates containing 50 µl allantoic fluid and 50 µl 0.5% chicken erythrocytes in saline. Results are presented as percent of positive lungs at a certain homogenates dilution ($10^{-8}$) as well as Log $EID_{50}$ (20).

Results

In light of the positive humoral and cellular immune response induced by the both $HA_{91-261}$ peptide and the corresponding DNA fragment $pHA_{91-261}$, the capacity of these agents to confer protective immunity against viral challenge was addressed. Following intranasal or intramuscular immunization, respectively, with peptide or DNA constructs (3 administration at 3 weeks intervals), mice were challenged with 1 HAU of influenza A/Texas/1/77 virus 1 month following the last boost. Five days later, animals were sacrificed and the presence of infectious virus in the lungs was determined. As shown in FIGS. 15a-b, mice immunized with either the DNA construct or the $HA_{91-261}$ peptide demonstrated significant level of protection (approaching 80%) against viral challenge, compared to non-immunized mice. The combined vaccination of DNA and peptide, however, did not induce protection even though it elicited significant cellular immune response against intact virus.

These results show that both peptide and DNA vaccinations generated according to the teachings of the present invention protect animals against viral infection.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES LIST

Additional References are Cited in the Text

1. Demichelli V., Jefferson T., Rivetti D., Deeks J. Prevention and early treatment of influenza in healthy adults. *Vaccine*, 18, 957-1030 (2000).
2. Wood A J., Prevention and treatment of influenza. The New England Journal of Medicine. 343, 1778-1787 (2000).
3. Gravenstein S., Davidson E H. Current strategies for management of influenza in the elderly population. *Clin. Infect. Diseases.* 35, 729-37 (2002).
4. Skehel J J., Cross K., Steinhauer D., Wiley D C. Influenza fusion peptides. *Biochem. Society Transactions.* 29, 623-26 (2001).
5. Skehel J J., Wiley D C. Receptor binding and membrane fusion in virus entry: The influenza hemagglutinin. *Annu. Rev. Biochem.* 69, 531-69 (2000).
6. Eckert D M., Kim P S. Mechanisms of viral membrane fusion and its inhibition. *Annu. Rev. Biochem.* 70, 777-810 (2001).
7. Ellington A D., Szostak J W., In vitro selection of RNA molecules that bind specific ligands. Nature, 346, 818-822 (1990).
8. Wagner R., Matrosovich M., Klenk H D. Functional balance between haemagglutinin and neuraminidase in influenza virus infection. *Rev. Med. Virol.* 12, 159-166 (2002)
9. Wilson I A., Skehel J J., Wiley D C. Structure of the haemagglutinin membrane glycoprotein of influenza virus at 3 A resolution. *Nature.* 289, 366-373 (1981).
10. Edwards M J., Dimmock N J. Hemagglutinin 1-specific immunoglobulin G and Fab molecules mediate post attachment neutralization of an early fusion event. *J Virol.* 75, 10208-10218 (2001).
11. Edwards M J., Dimmock N J. A haemagglutinin (HA1)-specific Fab neutralizes influenza A virus by inhibiting fusion activity. *J Virol.* 82, 1387-1395 (2001).
12. Edwards M J., Dimmock N J. Two influenza a virus-specific Fabs neutralize by inhibiting virus attachment to target cells, while neutralization by their IgGs is complex and occurs simultaneously through fusion inhibition and attachment inhibition. *Virology.* 278, 423-435 (2000).
13. Jeon S H., Arnon R Immunization with influenza virus hemagglutinin globular region containing the receptor-binding pocket. *Viral Immunol.* 15, 165-176, (2002).
14. Muller G M., Shapira M., Amon R. Anti-influenza response achieved by immunization with a synthetic conjugate. *Proc. Natl. Acad. Sci. USA.* 79, 569-573, (1982).
15. Amon R, Horwitz R J. Synthetic peptide based vaccines as vaccines. *Curr. Opin. Immunol.* 4, 449-53, (1992).
16. Tuerk C, Gold L. Systematic evolution of ligands by exponential enrichment: RNA ligands to bacteriophage T4 DNA polymerase. *Science.* 249, 505-510 (1990).
17. Sekkai D, Dausse E., Di Primo C., Darfeuille F., Boiziau C., Troulme J J. In vitro selection of DNA aptamers against the HIV-1 TAR RNA hairpin. *Antisense Nucleic Acid Drug Dev* 12, 265-71 (2002)

18. Matzura O., Wennborg A. RNA draw: an integrated program for RNA secondary structure calculation and analysiss under 32-bit Microsoft Windows. *Computer applications in the Biosciences.* 12, 247-249 (1996).
19. Levi R., Beear-Tzahar T., Arnon R. Microculture virus titration—a simple colourimetric assay for influenza virus titration. *J. Virol. Methods.* 52, 55-64 (1995).
20. Barret T., Inglis S C., Growth purification and titration influenza viruses, in virology: a practical approach (Ed. Mahy WJ) IRL pres, Washington D.C., pp. 119-151.
21. Gerhard W. The role of the antibody response in influenza virus infection, 171-190.
22. Mozdzanowska K., Furchner M., washko G., Mozdzanowski J., Gerhard W. A pulmonary influenza virus infection in SCID mice can be cured by treatment with hemagglutinin-specificantibodies that display very low virus-nutralizing activity in vitro. *J. Virol.* 71, 4347-4355 (1997).
23. Brown L E., Murray J M., White D O., Jackson D C. An analysis of the properties of monoclonal antibodies directed to epitopes on influenza virus hemagglutinin. *Arch. Virol.* 114, 1-26 (1990).
24. Vanlandschoot P., Beirnaert E., Barrere B., Calder L., Millar B., Wharton S., Minjou W., Fiers W. An antibody which binds to the membrane—proximal end of influenza virus haemagglutinin (H3 subtype) inhibits the low-pH-induced conformational change and cell-cell fusion but does not neutralize virus. *J. Gen. Virol.* 79, 1781-1791 (1990).
25. Brody E N., Gold L., Aptamers as therapeutic and diagnostic agents. *Reviews in Molecular Biotechnology,* 74, 5-13 (2000).
26. Hesselberth J., Robertson M P., Jhaveri S., Ellington A D., In vitroselection of nucleic acids for diagnostic applications. *Reviews in Molecular Biotechnology,* 74, 15-25 (2000).

What is claimed is:

1. A nucleic acid aptamer molecule comprising a polynucleotide sequence capable of specifically binding a polypeptide participating in influenza virus infection of cells, wherein said polynucleotide binds a region of hemagglutinin as defined by amino acid coordinates 91-261 of SEQ ID NO: 1, wherein the nucleic acid aptamer is capable of preventing influenza virus infection of cells in vitro and in vivo.

2. A pharmaceutical composition comprising as an active ingredient the nucleic acid molecule of claim 1 and a physiologically acceptable carrier.

3. The pharmaceutical composition of claim 2, further comprising an antiviral agent.

4. The pharmaceutical composition of claim 3, wherein said antiviral agent is conjugated to said nucleic acid molecule.

5. A composition of matter comprising an antiviral agent conjugated to the nucleic acid molecule of claim 1.

6. The nucleic acid molecule of claim 1, wherein said polynucleotide sequence is as set forth in SEQ ID No. 12.

7. The nucleic acid molecule of claim 1, wherein said polynucleotide sequence is single stranded.

8. The nucleic acid molecule of claim 1, wherein said polynucleotide sequence is DNA.

9. The nucleic acid molecule of claim 1, wherein said polynucleotide sequence is RNA.

10. The nucleic acid molecule of claim 1, wherein said nucleic acid molecule further comprising a detectable label.

11. The nucleic acid molecule of claim 1, wherein said polynucleotide sequence includes 2'-fluoro (2'-F) modified nucleotides.

12. The nucleic acid molecule of claim 1, wherein said polynucleotide sequence is selected having a length between 10 to 35 nucleotides.

* * * * *